United States Patent
Walsh et al.

(10) Patent No.: US 7,279,304 B2
(45) Date of Patent: Oct. 9, 2007

(54) METHODS FOR PREPARATION OF MACROCYCLIC MOLECULES AND MACROCYCLIC MOLECULES PREPARED THEREBY

(75) Inventors: Christopher Thomas Walsh, Wellesley, MA (US); John W. Trauger, Somerville, MA (US); Rahul Manu Kohli, Cambridge, MA (US); Michael D. Burkart, Boston, MA (US); Mohammed A. Maraheil, Marburg (DE); Henning Dieter Mootz, Haan (DE); Dirk Schwarzer, Marburg (DE)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/017,324

(22) Filed: Dec. 15, 2001

(65) Prior Publication Data

US 2002/0192773 A1     Dec. 19, 2002

Related U.S. Application Data

(60) Provisional application No. 60/332,763, filed on Nov. 6, 2001, provisional application No. 60/256,596, filed on Dec. 18, 2000.

(51) Int. Cl.
*C12P 1/00* (2006.01)
*C12P 21/06* (2006.01)

(52) U.S. Cl. .................. 435/41; 435/68.1; 435/135
(58) Field of Classification Search .............. 435/121
See application file for complete search history.

(56) References Cited

U.S. PATENT DOCUMENTS 5,847,121 A    12/1998  Yau et al.

5,883,293 A    3/1999  Gilon et al.

FOREIGN PATENT DOCUMENTS

WO      00/36093      6/2000

OTHER PUBLICATIONS

Trauger et al. Peptide cyclization catalysed by the thioesterase domain of tyrocidine synthetase. Nature. Sep. 2000. 407:215-218.*

Y. Xue et al. Nature, vol. 403 (2000) 571-575, "Alternative modular polyketide synthase expression controls macolactone structure."

L. Tang et al.Chem. & Biol. vol. 7 No. 2 (2000) 77-84, "Formation of functional heterologous complexes using subunits from the picromycin, erythromycin and oleandomycin polyketide synthases."

(Continued)

*Primary Examiner*—Nashaat T. Nashed
(74) *Attorney, Agent, or Firm*—George W. Neuner; Edwards Angell Palmer & Dodge LLP

(57)    ABSTRACT

The preparation of macrocyclic molecules from linear, synthetic thioester precursors is disclosed. An excised thioesterase domain isolated from either a polyketide synthases (PKS) or non-ribosomal peptide synthetases (NRPS) multido system catalyzes the cyclization reaction. Thioester substrates also are described that are efficiently cyclized by the method of the present invention. Additionally, macrocyclic molecules, including macrolactones and macrolactams, that are prepared by the macrocyclization methods of the invention are described.

56 Claims, 9 Drawing Sheets

OTHER PUBLICATIONS

R.McDaniel et al. Proc. Natl. Acad. Sci. USA vol. 96 (1999) 1846-1857, "Multiple gentic mofifications of the erythromycin polyketide snthase to produce a library of nove 'unnatural' natural products."

R. Gokhale et al. Chem. & Biol., "Mechanism and specificity of the terminal thioesterase domain from the erythromycin polyetide snthase."

C. Kao et al. J. Am. Chem. Soc. 119 (1997) pp. 1139-1140, "Gain of Functio Mutagenesis of the Erythromycin Polyketide Synthase. 2. Engineered Biosnthesis of an Eight-Membered Ring Tetraketide Lactone".

J.Jacobsen et al. Science vol. 277 (1997) 367-369) "Precursor-Directed Biosynthesis of Erythromycin Analogs by an Engineered Polytide Synthase".

J.Humphrey et al. Am. Chem. Soc. 97 (1997) pp. 2243-2266, "Chemical Synthesis of Natural Product Peptides: Coupling Methods for the Incorporation of Noncoded Amino Acids into Peptides."

T. Stachelhaus et al. Science vol. 269 (1995) pp. 69-72, "Rational Design of Peptide Antibiotics by Targeted Replacement of Bacterial and Fungal Domain".

J. Cortes et al. Science vol. 268 (1995)pp. 1487-1489, "Repositioning of a Domain a Modular Polyketide Synthase to Promote Specific Chain Cleavage".

R. Aggarwal, et al. Am. Chem. Soc. vol. 15 (1995) pp. 1517-1520. The Thioesterase of the Erythromycin-producing Polyketide Synthase: Mechanistic Studies in vitro to Investigate its Mode of Action and Substrate Specificity:.

* cited by examiner

US 7,279,304 B2

METHODS FOR PREPARATION OF MACROCYCLIC MOLECULES AND MACROCYCLIC MOLECULES PREPARED THEREBY

This application claims the benefit of U.S. Provisional Applications Ser. No. 60/256,596 filed Dec. 18, 2000 and 60/332,763 filed Nov. 6, 2001, the teachings of which are incorporated herein by reference.

This invention was made with government support under Grants AI 10507-02 and GM-20011 from the National Institute of Health. The government has certain rights in the invention.

FIELD OF INVENTION

The present invention relates to methods for the preparation of macrocyclic molecules and more particularly to macrocyclization of thioester substrates catalyzed by an excised Type 1 thioesterase (TE) domain. Utilizing this invention, macrocyclic molecules including many useful pharmaceuticals can be prepared using excised TE domains obviating traditional synthetic chemistry approaches to macrocyclic molecule synthesis, which generally exhibit low yields, require protecting groups and typically are carried out in organic solvents.

BACKGROUND OF THE INVENTION

An enormous range of medicinally important polyketide and peptide natural products assembled by modular polyketide synthases (PKSs), non-ribosomal peptide synthetases (NRPS) and mixed PKS/NRPS systems have macrocyclic structures, including the antibiotics erythromycin (PKS) and daptomycin (NRPS), the immunosuppressants cyclosporin (NRPS) and rapamycin (PKS/NRPS) and the antitumor agent epothilone (PKS/NRPS). PKSs and NRPSs are very large multifunctional proteins that are organized into sets of functional domains termed modules (Cane et al, *Science* (1998) 282:62-8; Marahiel et al, *Chem. Rev.* (1997) 97:2651-74). The sequence of modules corresponds directly to the structure of the product. Partially formed products are covalently tethered by thioester linkages to a carrier protein domain in each module. The thiol tether on each carrier domain is phosphopanetheine, which is attached to a conserved serine residue in the carrier protein in a post-translational priming reaction catalyzed by phosphopanetheinyl transferase (Lambalot et al, *Chem. Biol.* (1996) 3:923-36). Chain initiation involves loading a specific monomer onto each carrier protein's thiol tether. Subsequent chain elongation steps involve transfer of the growing chain from an upstream carrier protein to the adjacent downstream carrier protein-bound monomer. The full-length chain is almost always cyclized and released from the enzyme at the C-terminus of the NRPS or PKS system by a 28-35 kD TE domain (Cane et al, *Science* (1998) 282:62-8). During this final cyclization step, deacylation of the resulting acyl-O-TE intermediate at the C-terminal TE domain occurs either by intramolecular cyclization to form macrolactones or macrolactams or by hydrolysis.

The 6-deoxyerythronolide B synthase (DEBS) protein is a multidomain PKS protein with an integral TE domain that catalyzes cyclization of a protein-bound polyketide. Modification of domain identity or sequence in the natural DEBS protein by single or multiple domain substitutions or insertions of natural heterologous subunits generates DEBS protein variants that produce compounds with various ketide unit sequences. Systematic variation of the sequence of domains in the multidomain DEBS can in principle generate libraries of compounds (McDaniel et al, *PNAS*, (1999) 96:1846-51; McDaniel et al, *Chem Biol*, (2000) 7:77-84).

Kao disclosed the design and construction of engineered derivatives of the DEBS protein that is capable of synthesizing 6 and 8 member-ring lactones. The engineered DEBS derivatives included systems with protein modules, e.g. domains, exclusively from the DEBS system and hybrid derivatives that included protein modules from both the DEBS system and from the rapamycin PKS (RAPS) protein system. The DEBS-only derivative generated 6-member lactones and the DEBS-RAPS hybrid catalyzed the formation of a new 8-member lactone (Kao, *J. Am. Chem. Soc.* (1997) 119:11339-40).

The expression of a naturally occurring amino-terminal truncated form of a PKS protein to generate a macrocyclic molecule with smaller rings is described by Xue (Xue et al, *Nature*, (2000) 403:571-5). Truncation of the last condensation module from PikAIV in *S. venezuelae* leads to 'skipping' of the final condensation cycle in polyketide biosynthesis to generate a 12-membered ring macrolactone, 10-deoxymethynolide, instead of the 14-membered ring product molecule, narbonolide.

Jacobsen et al disclosed a method for producing a series of polyketides by blocking the first condensation step of the DEBS protein system and introducing exogenous synthetic engineered molecules. The synthetic methods using the blocked DEBS protein system resulted in the highly selective production of a variety of polyketide molecules including aromatic and ring-expanded variants of 6-deoxyerythronolide B (Jacobsen et al, *Science*, (1997) 277:367-9).

The DNA sequence encoding the TE domain from 6-deoxyerythonolide B synthase (DEBS) has been excised and independently expressed and the domain isolated either as isolated TE domain enzyme (Gokhale, *Chem Biol*, (1999) 6:117-25) or as part of an ACP-TE di-domain protein (Aggarwal, *J Chem Soc, Chem Comm*, (1995) 15:1519-20). Thioester substrates were exclusively hydrolyzed to corresponding carboxylic acids by both the isolated TE domain and the ACP-TE didomain. The ACP-TE di-domain further hydrolyzes aryl esters. No cyclization was observed in these systems.

Many useful pharmaceuticals have macrocyclic structures (a large ring composed of 10 or more atoms). Traditional synthetic chemistry approaches to the synthesis of macrocyclic compounds have drawbacks including, but not limited to, low yields of macrocyclic molecule products, protecting groups required to block or mask reactive functionalities, and the need to carry out reactions in organic solvents.

International Publication No. WO 00/36093 describes a method for producing cyclic peptides and splicing intermediates of peptides in a looped conformation. The methods utilize the trans-splicing ability of split inteins to catalyze cyclization of peptides interposed between two portions of a split intein. The interaction of the two portions of the split intein creates a catalytically active intein, which catalyzes the formation and liberation of a cyclic peptide product.

However, there remains an unfulfilled need for synthetic methods for preparing macrocyclic molecules in high yield without requiring functional group protection or carrying out reactions in organic solvents.

SUMMARY OF THE INVENTION

The present invention features a method of preparing macrocyclic molecules from linear precursors. More specifically, the present invention features a method for the cyclization of linear substrates wherein macrocyclic ring-closure is effected preferably by the formation of an amide or an ester bond catalyzed by a thioesterase domain excised and expressed from the DNA sequence for non-ribosomal peptide synthetase (NRPS) or polyketide synthase (PKS) multidomain proteins.

It is known that an integrally bound TE domain in a multidomain PKS or NRPS system catalyzes macrocyclization of protein-bound thioester substrates. However, applicants have discovered that excised TE domains can catalyze macrocycle formation using synthetic substrates. An enzymatic approach to macrocyclic molecule synthesis has advantages over traditional synthetic chemistry approaches including (i) high yield, (ii) regioselective cyclization that eliminates the need for protecting groups and (iii) reaction in aqueous systems.

A method for the preparation of a macrocyclic molecule comprises the step of contacting purified excised TE domain protein with a substrate that comprises a compound having an activated acyl residue and a pendant nucleophile separated by a linear backbone under conditions conducive to formation of a TE-O-acyl bond such that the pendant intramolecular nucleophile can displace the TE domain to form the macrocyclic molecule.

In preferred embodiments, the macrocyclization methods of the invention are carried out using substrates having an activated ester functional group or an activated thioester functional group as the activated acyl residue.

In preferred embodiments, the macrocyclization methods of the invention are carried out in an essentially aqueous medium that optionally includes one or more buffers and/or other organic or inorganic salts. Further, the buffered aqueous reaction medium preferably has a pH of about 5 to about 9, more preferably a pH of about 6 to about 8 and most preferably the reaction medium is essentially neutral with a pH of about 7. Preferred buffer additives include 3-(N-morpholino)propanesulfonic acid (MOPS) and other buffers that function well at or around neutral pH.

In preferred embodiments of the invention, the rate of the macrocyclization reaction catalyzed by an excised thioesterase domain protein is in the range of about 1 to about 100 macrocyclization reactions per minute per enzyme molecule. Useful amounts of macrocyclic compounds, e.g. about 1 μg or more of a macrocyclic compound, can be prepared with reaction times ranging from about 1 minute to about 120 minutes. The amount of hydrolysis byproduct is preferably less than the amount of the macrorocylization product, more preferably less than 50 wt % of the amount of the macrocyclization product molecule. In particularly preferred macrocyclization reactions catalyzed by an excised thioesterase domain protein, the amount of hydrolysis byproduct is less than about 25 wt % of the amount of the macrocyclization product molecule.

Preferred ring sizes of macrocyclic compounds produced by macrocyclization catalyzed by an excised thioesterase domain protein of the present invention comprise from about 12 to about 60 atoms. More specifically, for peptidic substrates of the invention preferred ring sizes comprise from 4 to about 20 amino acid residues.

Preferably, macrocyclization substrates suitable for macrocyclization catalyzed by an excised thioesterase domain protein in accord with this invention are soluble in buffered or unbuffered aqueous solutions, or in aqueous solutions comprising a small amount, e.g. less than or equal to 20% v/v, of an organic solvent, at concentrations of at least about 0.1 gram of substrate per liter (g/L). Preferred organic solvents that are suitable for use in the present invention include sulfoxides, esters, amides and the like such as, e.g., dimethylformamide (DMF) and dimethylsulfoxide (DMSO).

The present invention provides a substrate for macrocyclization catalyzed by an excised TE domain protein according to formula (I):

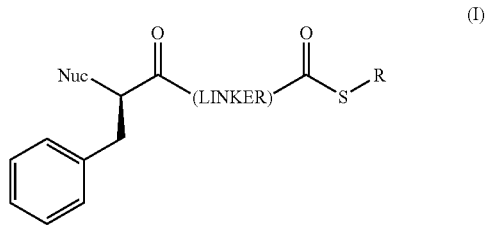

wherein:
Nuc is either $NH_2$ or OH;
LINKER is a group connecting the thioester and nucleophile that comprises a linear backbone of at least 14 atoms; and
R is a lower hydrocarbon group that can be substituted.

Preferably, the substrate is sufficiently polar such that its solubility and that of the resulting macrocyclic molecule in the aqueous reaction medium is at least 0.1 g/L, preferably at least 1 g/L, and more preferably at least 10 g/L.

The present invention also provides a macrocyclic molecule according to Formula (II) is prepared by an excised TE domain protein catalyzed cyclization of substrates according to formula (I).

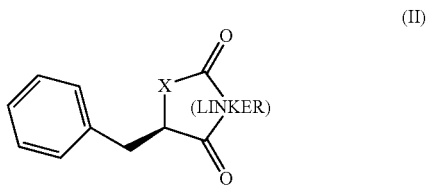

wherein:
LINKER is defined as in Formula (I); and
X is chosen from S, O, and NH.

In accord with the present invention, an excised TE domain protein catalyzes the macrocyclization of a family of substrates having the end group functionality of the natural substrate for the TE domain protein. Specific examples describe the use of TE domain protein excised from the Tyrocidine NRPS multidomain enzyme and from the surfactin synthetase multidomain enzyme to catalyze macrocyclization of substrates. However, the use of other excised TE domain proteins from other NRPS multidomain enzymes or from PKS multidomain enzymes that are appropriate to catalyze the macrocyclization of other substrates are also included in the scope of the present invention. The substrate specificity of other excised TE domain proteins can be determined by those skilled in the art by routine procedures analogous to the determination of substrate specificity for excised TycC TE domain protein disclosed herein. An appropriate excised TE domain protein can be chosen to catalyze the macrocyclization of a specified substrate based on structure commonalties between the specified substrate and the wild-type substrate of a particular TE domain protein. For example, excised TE domain proteins from PKS multidomain enzymes are preferable catalysts for the macrocyclization of polyketide substrates and excised TE domain proteins from NRPS multidomain enzymes are preferable for polypeptide substrates or substrates that comprise one or more peptide sequences.

In specific embodiments of the present invention, the TE domain from tyrocidine NRPS (FIG. 2A), which as part of a multidomain NRPS enzyme catalyzes in nature the assembly of the cyclic decapeptide antibiotic tyrocidine A, can independently catalyze cyclization of thioester substrates according to Formula (I) after excision from the multidomain enzyme system. The linker group can be, e.g., the nine C-terminal amino acid residues of the natural tyrocidine A decapeptide substrate. Further acceptable substrate linkers can comprise depsipeptides (peptides in which one or more backbone amide bonds is replaced with an ester bond), a variable number of amino acid residues, synthetic non-peptidic spacers or a combination of one or more of the above groups, or the like. Additionally, substrates according to Formula (I) where Nuc is OH also are cyclized by methods of the invention resulting in macrolactone formation.

In other embodiments of the present invention, the TE domain from the surfactin NRPS, which as part of a multidomain NRPS enzyme catalyzes in nature the assembly of the cyclic lipopeptide antibiotic surfactin, can independently catalyze cyclization of thioester substrates according to Formula (III) after excision from the multidomain enzyme system. The linker can be any sequence of six or more amino acids, and can also comprise depsipeptides, variable number of amino acid residues, synthetic non-peptidic spacers or a combination of one or more of the above groups, or the like.

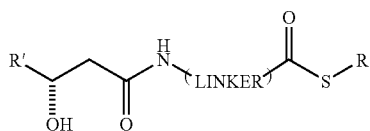

(III)

wherein:
LINKER is a group connecting the thioester and nucleophile that comprises a linear backbone of at least 14 atoms; and
R is a lower alkyl group that can be substituted.

The present invention also provides a macrocyclic molecule according to Formula (III) is prepared by an excised TE domain protein catalyzed cyclization of substrates according to formula (IV).

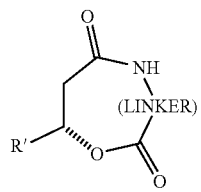

(IV)

wherein:
LINKER is a group connecting the thioester and nucleophile that comprises a linear backbone of at least 14 atoms; and
R is a lower hydrocarbon group that can be substituted.

The invention also provides a method to cyclize, catalyzed by the excised TE domain protein, substrates with a variable number of amino acid residues. For example, for the TE domain excised from the tyrocidine NRPS, thioester substrates comprising at least 6 amino acid residues that include a key recognition end group residue are cyclized by the TE domain protein. Preferable substrates have between about 7 and about 16 amino acid residues.

The invention also provides a method for the macrocyclization of substrates wherein the macrocyclic ring formed can include both synthetic and biosynthetic amino acid residues, amino acid analogs, peptidomimetic components and one or more domains of non-peptidic, non-peptidomemetic linkers, and the like. Preferred substrates include (i) the N-terminal recognition residue, for example, D-phenylalanyl or D-3-phenyl-lactyl, (ii) a polar linker that imparts sufficient aqueous solubility, and (iii) a C-terminal thioester activated acyl group. The non-peptidic spacers comprise functional groups appropriate for formation of ester or amide bond linkages with optional peptide sequences, the N-terminal recognition residue or the C-terminal thioester activated acyl group. Preferably, the linker domains comprise functional groups that are sufficiently flexible to facilitate substrate macrocyclization by the methods of the present invention.

In certain preferred embodiments, an excised TE domain protein can catalyze sequence elongation of two linear molecules as well as cyclization. Preferred substrates for a cascade elongation-cyclization reaction are substrates according to formula (I) where the linker is insufficiently long to permit cyclization of the substrate monomer by a TE domain protein catalyzed process. Formation of an amide or ester bond by intermolecular attack from a second unbound substrate monomer on the TE-O-acyl substrate monomer bond results in substrate elongation, e.g., a substrate dimer that has a linear backbone twice the length of the substrate monomer. Additional elongation reactions can occur as needed until the substrate dimer molecule or oligomer is sufficiently long so that the intramolecular nucleophile, Nuc, of the intermediate TE domain substrate dimer or oligomer complex can attack the TE-O-acyl bond to form a macrocyclic product. For example, a pentapeptide substrate typically is not long enough to undergo macrocyclization. Dissociation of the TE domain bound pentapeptide occurs by intermolecular nucleophilic attack of the N-terminal amine functional group from a second pentapeptide substrate to generate a decapeptide substrate dimer that has a sufficiently long linear backbone for TE domain protein catalyzed macrocyclization of the decapeptide substrate dimer. Alternatively, the peptide linkage formed in substrate elongation can link different monomers. Two different substrates can be heterodimerized by the TE-catalyzed elongation process generating a linear molecule which may undergo subsequent cyclization.

Definitions

As used herein, the terms "excised thioesterase domain protein" or "excised TE domain protein" or "excised TE domain" refer to a protein domain normally present as the last domain in a large, multidomain polyketide synthase (PKS) or in non-ribosomal peptide synthetase (NRPS) proteins that normally catalyze in nature cyclization of a protein-bound thioester intermediate assembled by the upstream domains. For example, the term "excised TE domain protein" includes excised and expressed TycC TE from the tyrocidine NRPS (Trauger, Nature (2000) 407: 215-218) and also other Type I TE domain proteins in nature that are homologous to or provide function similar to the TE domain protein from the tyrocidine synthetase including gramicidin synthetase TE, surfactin synthetase TE, bacitracin synthetase TE, fengycin synthetase TE, calcium-dependent antibiotic (CDA) synthetase TE, microcystin synthetase TE, epothilone synthetase TE, daptomycin synthetase TE, syringomycin synthetase TE, nystatin synthetase TE, lichenysin synthetase TE, 6-deoxyerythronolide B synthase (DEBS), and the like.

Excised TE domain protein also includes peptide sequences that are shorter than the complete, naturally occurring TE domain-containing NRPS or PKS protein but are longer than the TE domain peptide sequence, provided that the increased length of the peptide sequence does not prevent excised TE domain protein macrocyclization activity. Thus, the phrase "excised" refers to one or more domains of a multidomain protein system that have been isolated and expressed independently of the natural multidomain protein system. In practice, excised TE domain proteins generally are prepared by (i) isolating the part of the DNA that encodes the excised TE domain from the DNA encoding the TE-containing NRPS or PKS protein, (ii) expressing the DNA encoding the excised TE domain in a suitable expression host, e.g. in the bacterium *Eschercia coli* and (iii) purifying the expressed excised TE domain protein. Non-natural peptide sequences also can be included in the excised TE domain protein sequence to facilitate expression or purification of the excised TE domain protein. Typically, such excised TE domain proteins have a molecular weight less than about 100 kilodaltons (kD). For excised TE domain protein from a multidomain NRPS or PKS system that catalyzes substrate cyclization, preferred TE domain peptide sequences are in the range of about 27-35 kD.

As used herein, the phrases "key recognition residue" and "recognition residue" refer to the groups in a substrate that are necessary for macrocyclization to occur. In general, most key recognition residues are located near the portions of the substrate that react to form the macrocycle, e.g., near the N- and C-terminal ends of peptide substrates for the TE domain from the tyrocidine synthetase. In typical examples, the substrate groups near the nucleophile that reacts with the acyl-O-TE intermediate are key recognition residues that are necessary for TE domain catalyzed substrate macrocyclization to occur.

As used herein, the phrase "an amino acid side chain" refers to the distinguishing substituent attached to the α-carbon of an amino acid; such distinguishing groups are well known to those skilled in the art. For instance, for the amino acid glycine, the side chain is H; for the amino acid alanine, the side chain is $CH_3$, and so on.

As used herein, the term "amino acid" is intended to include common natural or synthetic amino acids and common derivatives thereof, known to those skilled in the art. Typical amino-acid symbols denote the L configuration unless otherwise indicated by a D appearing before the symbol.

The substrates herein described can have asymmetric centers or axes. All chiral, diastereomeric, and racemic forms are included in the present invention. Many geometric isomers of olefins and the like also can be present in the compounds described herein, and all such stable isomers are contemplated in the present invention.

The term "substituted", as used herein, means that any one or more hydrogens on the designated atom is replaced with a group selected from the defined list, provided that the designated atom's normal valence is not exceeded, and that the substitution results in a stable compound. When a substituent is keto (i.e., =0), then 2 hydrogens on the atom are replaced. Keto substituents are not directly attached to aromatic ring atoms.

When any variable occurs more than one time in any constituent or formula for a compound, its definition at each occurrence is independent of its definition at every other occurrence. Thus, for example, if a group is shown to be substituted with 0-2 R*, then said group may optionally be substituted with up to two R* groups and R* at each occurrence is selected independently from the definition of R*. Also, combinations of substituents and/or variables are permissible provided that such combinations result in stable compounds.

As indicated herein, various substituents of the compounds of the present invention and various formulae set forth herein are "optionally substituted", including, e.g., a linker or carboxylate leaving group. When substituted, those substituents can be substituted at one or more of any of the available positions, typically 1, 2, 3, 4, or 5 positions, by one or more suitable groups such as those disclosed herein.

Suitable groups or "substituted" moieties for hydrogen atoms in compounds of the invention include, e.g., halogen such as fluoro, chloro, bromo or iodo; cyano; hydroxyl; nitro; azido; alkanoyl, such as a $C_{1-6}$ alkanoyl group such as acyl and the like; carboxamido; alkyl groups including those groups having 1 to about 12 carbon atoms, preferably 1-6 carbon atoms; alkenyl and alkynyl groups including groups having one or more unsaturated linkages and from 2 to about 12 carbon atoms, preferably 2-6 carbon atoms; alkoxy groups including those having one or more oxygen linkages and from 1 to about 12 carbon atoms, preferably 1-6 carbon atoms; aryloxy groups such as phenoxy and benzyloxy; alkylthio groups including those moieties having one or more thioether linkages and from 1 to about 12 carbon atoms, preferably 1-6 carbon atoms; alkylsulfinyl groups including those moieties having one or more sulfinyl linkages and from 1 to about 12 carbon atoms, preferably 1-6 carbon atoms; alkylsulfonyl groups including those moieties having one or more sulfonyl linkages and from 1 to about 12 carbon atoms, preferably 1-6 carbon atoms; aminoalkyl groups such as groups having one or more N atoms and from 1 to about 12 carbon atoms, preferably 1-6 carbon atoms; carbocyclic aryl groups having 6 or more carbons, particularly phenyl and benzyl (e.g., wherein an Ar group can be substituted or unsubstituted biphenyl moiety); arylalkyl having 1 to 3 separate or fused rings and from 6 to about 18 carbon ring atoms, with benzyl being a preferred group; arylalkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, 0 or S atoms.

As used herein, "alkyl" is intended to include both branched and straight-chain saturated aliphatic hydrocarbon groups, having the specified number of carbon atoms. Examples of alkyl include, but are not limited to, methyl, ethyl, n-propyl, i-propyl, n-butyl, s-butyl, t-butyl, n-pentyl, and s-pentyl. Preferred alkyl groups are lower alkyl groups having from 1 to about 6 carbon atoms. The term $C_{1-6}$ alkyl as used herein means alkyl groups consisting of 1 to 6 carbon atoms, which may contain a cyclopropyl moiety.

"Cycloalkyl" is intended to include saturated ring groups, having a specified number of carbon atoms, such as cyclopropyl, cyclobutyl, cyclopentyl, or cyclohexyl and bridged or caged saturated ring groups such as norbornane or adamantane and the like. Preferred cycloalkyl groups are cycloalkyl groups having from 3 to about 8 ring atoms. The term $C_{3-8}$ cycloalkyl as used herein means cycloalkyl groups consisting of a aliphatic ring with 3 to 8 atoms in the ring.

"Alkenyl" is intended to include hydrocarbon chains of either a straight or branched configuration comprising one or more unsaturated carbon-carbon bonds, which may occur in any stable point along the chain such as, e.g., ethenyl and propenyl. Preferred alkenyl groups resare lower alkenyl groups having from 2 to about 6 carbon atoms. The term $C_{2-6}$ alkenyl as used herein means alkenyl groups consisting of 2 to 6 carbon atoms.

"Alkynyl" is intended to include hydrocarbon chains of either a straight or branched configuration comprising one or more triple carbon-carbon bonds that may occur in any stable point along the chain such as, e.g., ethynyl and propynyl. Preferred alkynyl groups are lower alkynyl groups having from 2 to about 6 carbon atoms. The term $C_{2-6}$ alkynyl as used herein means alkynyl groups consisting of 2 to 6 carbon atoms.

"Haloalkyl" is intended to include both branched and straight-chain saturated aliphatic hydrocarbon groups having the specified number of carbon atoms, substituted with 1 or more halogen (for example $-C_v(X^i)_{wi}(H_{2v+1-\Sigma(wi)})$ where v=1 to 6; $X^i$=F(i=1), Cl(i=2), Br(i=3), I(i=4) and $\Sigma w_I \leq 2v+1$). Examples of haloalkyl include, but are not limited to, trifluoromethyl, trichloromethyl, pentafluoroethyl, and pentachloroethyl. Preferred haloalkyl groups are lower halolkyl groups having from 1 to about 6 carbon atoms. The term $C_{1-6}$ haloalkyl as used herein means haloalkyl groups consisting of 1 to 6 carbon atoms.

As used herein, the term "hydrocarbon group" is intended to include alkyl, cycloalkyl, alkenyl, alkynyl, and aryl groups or a group that comprises a combination of two or more alkyl, cycloalkyl, alkenyl, alkynyl or aryl group regions. Hydrocarbon groups may further comprise heteroatoms such as N, O, F, Si, S, Cl, Br and the like. Preferably, hydrocarbon groups have from 0 to about 3 heteroatoms. The term lower hydrocarbon group as used herein means a hydrocarbon group consisting of 1 to 6 carbon atoms which may include 1, 2, or 3 heteroatoms.

As used herein, the term "lipophilic group" refers to any hydrophobic group that is soluble in or miscible with lipids, hydrocarbons and other hydrophobic materials. Examples of lipophilic groups include, but are not limited to, long-chain $C_6$-$C_{32}$ alkyl groups that include linear alkyls, branched alkyls with one or more branch points or linear or branched alkyls which include one or more $C_3$-$C_8$ cycloalkane groups, long-chain $C_6$-$C_{32}$ alkenyl groups with one or more C—C double bonds that include linear alkenyls, branched alkenyls with one or more branch points or linear or branched alkenyls which include one or more $C_3$-$C_8$ cycloalkane or cycloalkene groups, long-chain $C_6$-$C_{32}$ alkynyl groups with one or more C—C triple bonds that include linear alkynyls, branched alkynyls with one or more branch points or linear or branched alkynyls which include one or more $C_3$-$C_8$ cycloalkane groups or long-chain $C_6$-$C_{32}$ alkyl, alkenyl or alkynyl groups that are optionally substituted with aryl, halogen, alkoxy, mono- or di($C_1$-$C_6$)amino, $C_1$-$C_6$-alkyl ester.

As used herein, the term "cyclic lipopeptide" refers to cyclic peptides or cyclic depsipeptides that include one or more lipophilic groups, as well as cyclic peptides or depsipeptides that include one or more non-peptidic groups and one or more lipophilic groups.

"Alkoxy" means an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Preferred alkoxy groups are lower alkoxy groups having from 1 to about 6 carbon atoms.

The term "halogen" means fluorine, chlorine, bromine, or iodine.

DETAILED DESCRIPTION OF THE INVENTION INCLUDING PREFERRED EMBODIMENTS

Figure 1:
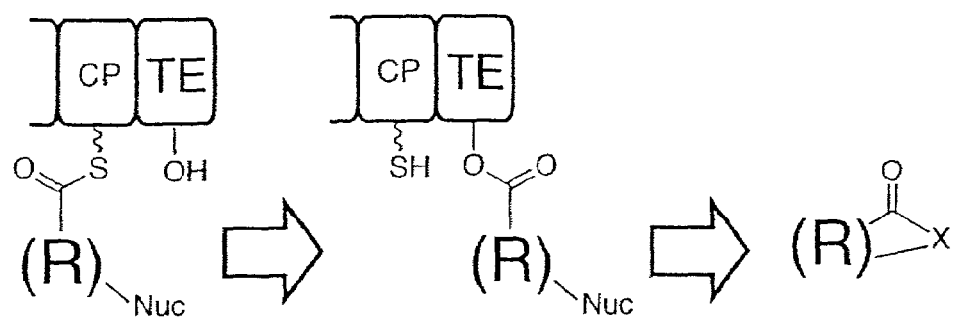
FIG. 1(a) is a systematic illustration of the reaction scheme for a TE-catalyzed cyclization in the natural context of an intact NRPS or PKS multidomain protein.
FIG. 1(b) is a systematic illustration of the reaction scheme for the TE-catalyzed macrocyclization in accord with the present invention.
Figure 1:
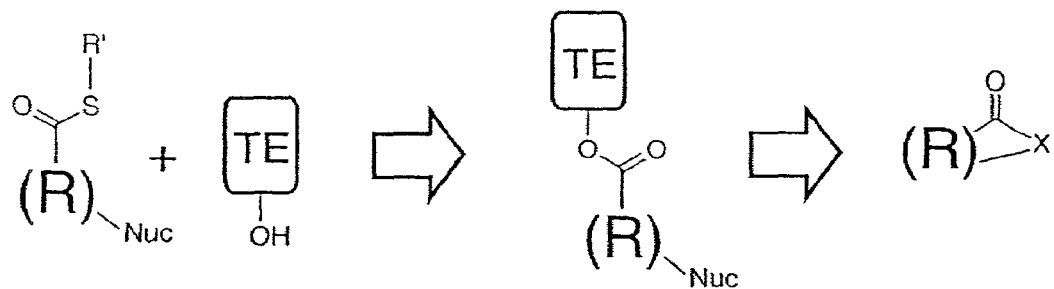

The present invention provides a method for macrocyclic molecule synthesis that involves the use of an excised thioesterase (TE) domain protein from a non-ribosomal peptide synthetase (NRPS) or polyketide synthase (PKS) multidomain protein systems to catalyze the cyclization of synthetic substrates. The method is useful for a wide variety of substrates, including substrates that differ from a wild-type TE domain substrate. This macrocyclization method is a generally useful procedure for the preparation of a wide range of macrocyclic molecules including pharmaceutical agents or libraries of macrocyclic molecules.

In accord with the present invention, the preparation of macrocyclic molecules comprises contacting purified excised TE domain protein with a substrate molecule that is to be cyclized. The substrate molecule typically comprises an activated acyl residue and a pendant nucleophile separated by a linear backbone. The excised TE domain protein and substrate are contacted under conditions conducive to formation of a TE-O-acyl bond such that subsequently the pendant intramolecular nucleophile can displace the TE domain to form the macrocyclic product. Examples of suitable substrate molecules for macrocyclization catalyzed by the excised TE domain from tyrocidine synthetase are included in compounds represented by Formula I. Examples of suitable substrate molecules for macrocyclization catalyzed by the excised TE domain from surfactin synthetase are included in compounds represented by Formula III.

Other substrate molecules are suitable for macrocyclization by excised TE domain proteins originating from other NRPS or PKS multidomain systems. Specific examples of the invention describe the use of TE domain protein excised from the Tyrocidine A NRPS multidomain enzyme and or from the surfactin synthetase multidomain enzyme (see Example 21) to catalyze macrocyclization of substrate molecules. However, the use of other excised TE domain proteins that can be used to catalyze the macrocyclization of other substrates. An appropriate excised TE domain protein can be chosen to catalyze a specified substrate based on structure commonalties between the specified substrate and the wild-type substrate of a particular TE domain protein. For example, excised TE domain proteins from PKS multidomain enzymes are preferable catalysts for the macrocyclization of polyketide substrates and excised TE domain proteins from NRPS multidomain enzymes are preferable for polypeptide substrates or substrates that comprise one or more peptide sequences. Suitable excised TE domain proteins for use in the present invention include, but are not limited to tyrocidine synthetase TE, gramicidin synthetase TE, surfactin synthetase TE, bacitracin synthestase TE, fengycin synthetase TE, calcium-dependent antibiotic (CDA) synthetase TE, microcystin synthetase TE, epothilone synthetase TE, daptomycin synthetase TE, syringomycin synthetase TE, nystatin synthetase TE, lichenysin synthetase TE, 6-deoxyerythronolide B synthase (DEBS) and the like.

In preferred embodiments, TE domain protein catalyzed macrocyclization reactions are carried out in an aqueous medium. The aqueous medium also can comprise buffers such as 3-(N-morpholino)propanesulfonic acid (MOPS) and the like so that the aqueous solution has a pH between about 6 and about 9. Preferably, the pH is between about 6.5 and about 8. Particularly preferred are methods wherein the macrocyclization is carried out in about pH 7 aqueous medium.

Organic co-solvents are tolerated by the macrocyclization method where the organic solvent or a solution of two or more organic solvents is less than about 20% v/v of the solution. Preferably, the organic solution is less than about 10%, 5%, 2% or 1% v/v of the aqueous solution. Preferred organic solvent additives or organic co-solvents, if utilized, are miscible with water at the % v/v of the aqueous solution and are poor nucleophiles so that the organic solvent generally does not compete with the intramolecular nucleophile at displacing the TE-O-acyl bond. Preferable organic co-solvents are dimethylsulfoxide (DMSO), N,N-dimethyl-formamide (DMF) and other polar, weakly nucleophilic organic liquids.

Macrocyclization reactions are preferably carried out in a medium that solvates the substrate and the macrocyclic molecule generated in the cyclization reaction, typically water. Preferably, the solubility of the macrocyclization substrate and macrocyclic molecule product in the reaction mixture is at least about 0.1 g/L. More preferably, the solubility of the macrocyclization substrate and macrocyclic molecule product in the reaction mixture is at least about 1 g/L.

The quantity of catalyst used depends upon the rate of catalysis for a particular substrate, the volume of solution and other environmental factors. Typical catalyst loadings are less than about 20 mole % based on the moles of substrate. Preferred catalyst loadings are less than about 10 mole %, more preferably less than about 5 mole %. Particularly preferred ranges of catalyst loading are about 0.1 to about 2 mole %, more preferably from about 0.1 to about 1 mole %.

Preferably, macrocyclization reactions in accord with the present invention are performed at about room temperature, i.e., 20-25° C. However, the temperature can be varied as long as the TE domain protein is sufficiently stable and active.

Macrocyclization reactions of the present invention typically are complete in about 0.5 minutes to about 2 hours. Preferably, macrocyclization reactions are complete in less than about 1 hour. More preferably, macrocyclization reactions are complete in less than about 5 minutes.

Macrocyclization substrates are preferably cyclized by the excised TE domain protein having a rate constant ($k_{cat}$) that is at least about 1 cyclization reaction per minute per enzyme molecule. Macrocyclization substrates are more preferably cyclized by the excised TE domain protein having a rate constant ($k_{cat}$) that is at least about 10 cyclization reactions per minute per enzyme molecule.

The term $K_M$ is defined as the concentration at which the observed rate of cyclization is equal to one-half the maximum observed rate of cyclization. Macrocyclization substrates are preferably cyclized by the excised TE domain protein at a rate equal to one-half the maximum rate at a concentration of less than 1 mM (i.e., $K_M$<1 mM). Macrocyclization substrates are more preferably cyclized by the excised TE domain protein at a rate equal to one-half the maximum rate at a concentration of less than 0.1 mM (i.e. $K_M$<0.1 mM).

A suitable substrate for macrocyclization catalyzed by an excised TycC TE domain protein is represented by formula (I):

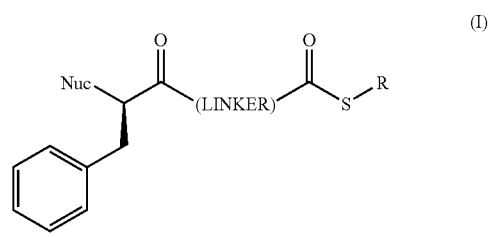

wherein:

Nuc is chosen from $NH_2$, OH or SH;

LINKER is a group of atoms or functional group residues connecting the thioester and the 2-(Nuc)-3-phenyl-propionyl residue, the LINKER comprises a linear backbone chain of at least about 14 atoms; and R is a lower hydrocarbon group that can be substituted.

Preferably, the substrate is sufficiently polar such that its solubility and that of the resulting macrocyclic molecule in the aqueous reaction medium is at least 0.1 g/L, preferably at least 1 g/L, and more preferably at least 10 g/L.

Preferable R groups are N-C$_2$-C$_6$alkanoylC$_2$-C$_6$aminoalkyl. More preferably, the R group is a N-acetylC$_2$-C$_6$aminoalkyl and a particularly preferable R group is N-acetylaminoethyl (e.g., SR together preferably is N-acetylcysteamine, SNAC).

Another suitable substrate for macrocyclization catalyzed by an excised TycC TE domain protein is represented by formula (I-A):

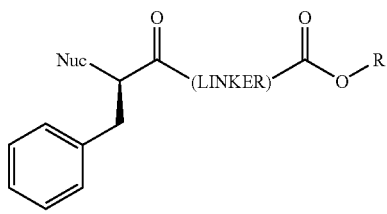

(I-A)

wherein

Nuc is chosen from NH$_2$, OH or SH;

LINKER is a peptidic sequence, synthetic hydrocarbon group or a combination thereof connecting the thioester and the 2-(Nuc)-3-phenyl-propionyl residue, the LINKER comprises a linear backbone of at least 14 atoms; and R is a group that can be represented by the formula:

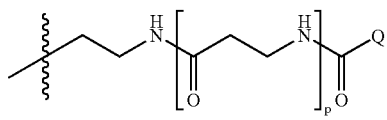

wherein Q is a group having between about 4 carbon atoms and about 20 carbon atoms and between about 0 and 10 hetero atoms selected from N, O or S, which can optionally be tethered to a solid support, where each carbon of the linear backbone may be optionally substituted with 0, 1, or 2 groups selected from C$_{1-6}$alkyl, hydroxy, amino, halogen, C$_{1-6}$alkoxy, or oxo; and p is an integer from 0 to about 2.

A macrocyclic molecule according to Formula (II) is prepared by excised TE domain protein catalyzed cyclization of substrates according to Formula (I) for Formula (I-A)

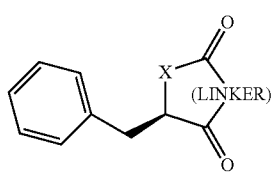

(II)

wherein:

LINKER is defined as in Formula (I); and

X is chosen from S, O, and NH.

Substrates useful in the practice of this invention include substrate molecules according to Formula (I) wherein the thioester is attached to a linker such that the C-terminus of the substrate is a dipeptide according to Formula (V):

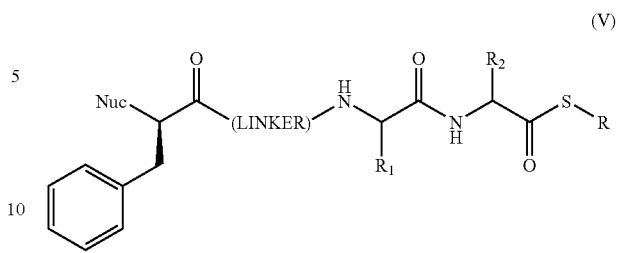

(V)

wherein Nuc, LINKER and R are defined as in Formula (I); and

R$_1$ and R$_2$ are chosen from the side chain substituents of the synthetic and biosynthetic amino acid side chain residues and each residue can have either D or L stereoconfiguration. R$_1$ and R$_2$ are chosen independently and can be the same or different.

Preferably, the substrate is sufficiently polar such that its solubility and that of the resulting macrocyclic molecule in the aqueous reaction medium is at least 0.1 g/L, preferably at least 1 g/L, and more preferably at least 10 g/L.

In preferred embodiments, a substrate according to Formula (V) further comprises a dipeptide in which R$_1$ comprises a group that is charged at pH 7. Preferably, R$_1$ is an optionally substituted ω-amino-C$_1$-C$_6$alkyl or a charged side chain from a biosynthetic amino acid. Particularly preferred are substrates where R$_1$ is the side chain from ornithine.

Also preferred are substrates according to Formula (V) where R$_2$ is an optionally substituted C$_1$-C$_6$ alkyl group or a linear or branched C$_1$-C$_6$ alkyl group. More preferably, R$_2$ is a linear or branched C$_1$-C$_6$ alkyl group.

Particularly preferred R groups in Formula (V) are N-C$_2$-C$_6$alkanoylC$_2$-C$_6$aminoalkyl. Most preferably, the R group is a N-acetylC$_2$-C$_6$aminoalkyl, particularly N-acetylaminoethyl (e.g., SR together is N-acetylcysteamine, SNAC).

Preferably, the substrate is sufficiently polar such that its solubility and that of the resulting macrocyclic molecule in the aqueous reaction medium is at least 0.1 g/L, preferably at least 1 g/L, and more preferably at least 10 g/L.

A macrocyclic molecule according to Formula (VI) is prepared by excised TE domain protein catalyzed cyclization of substrates according to formula (V).

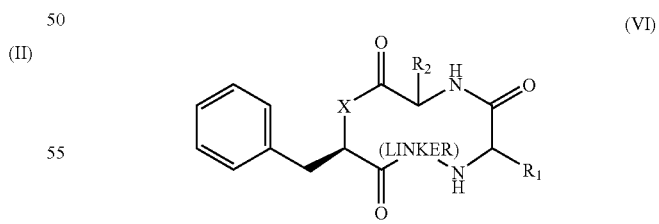

(VI)

wherein:

LINKER, R$_1$ and R$_2$ are defined as in Formula (I); and

X is chosen from S, O, and NH.

Another substrate useful in the practice of the present invention is a compound of Formula (I) in which each residue is connected by either an amide or ester bond as shown in Formula (VII):

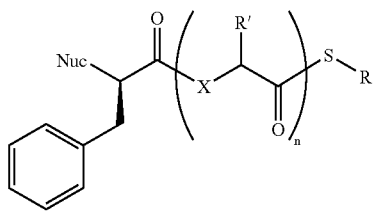

(VII)

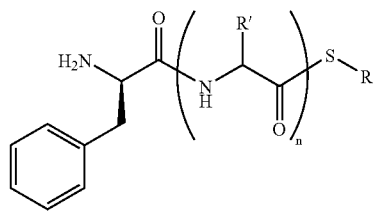

(IX)

wherein:

Nuc is chosen from $NH_2$ or OH;

n is an integral number greater than or equal to 5;

X is independently chosen for each occurrence of X in Formula (VII) from O and NH; and R is the same as defined in Formula (I);

each R' is independently chosen for each occurrence for R' in Formula (VII) from the side chain substituents of the synthetic and biosynthetic amino acid side chain residues and each residue can have either D or L stereoconfiguration.

Preferred R groups in Formula (VII) are optionally substituted $N-C_2-C_6$alkanoyl$C_2-C_6$aminoalkyl. More preferably, the R group is a $N$-acetyl$C_2-C_6$aminoalkyl and a particularly preferred R group is N-acetylaminoethyl (e.g., SR together is N-acetylcysteamine, SNAC).

Preferably, the substrate is sufficiently polar such that its solubility and that of the resulting macrocyclic molecule in the aqueous reaction medium is at least 0.1 g/L, preferably at least 1 g/L, and more preferably at least 10 g/L.

Macrocyclic molecules according to Formula (VIII) are prepared by excised TE domain protein catalyzed macrocyclization of substrate molecules according to formula (VII).

wherein:

n is an integral number greater or equal to 5;

R is as defined in Formula (I); and each R' is independently chosen for each occurrence for R' in Formula (IX) from the side chain substituents of the synthetic and biosynthetic amino acid side chain residues and each residue can have either D or L stereoconfiguration.

Preferred R groups in Formula (IX) are optionally substituted $N-C_2-C_6$alkanoyl$C_2-C_6$aminoalkyl. More preferably, the R group is a $N$-acetyl$C_2-C_6$aminoalkyl and a particularly preferred R group is N-acetylaminoethyl (e.g., SR together is N-acetylcysteamine, SNAC).

Preferably, the substrate is sufficiently polar such that its solubility and that of the resulting macrocyclic molecule in the aqueous reaction medium is at least 0.1 g/L, preferably at least 1 g/L, and more preferably at least 10 g/L.

A macrocyclic molecule according to Formula (X) is prepared by excised TE domain protein catalyzed cyclization of substrates according to formula (IX).

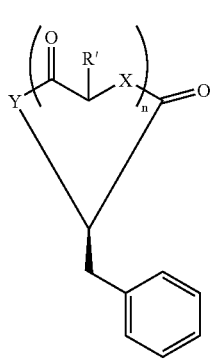

(VIII)

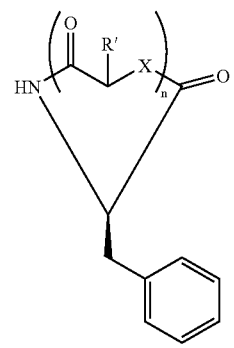

(X)

wherein:

X, n and R' are defined as in Formula (VII); and

Y is chosen from O and NH.

A preferred substrate according to Formula (VII) wherein the (R)-2-nucleophile-3-aryl-propionate functionality wherein:

X, n and R' are defined as in Formula (IX).

Another substrate according to Formula (VII) in which the (R)-2-nucleophile-3-aryl-propionate functionality nucleophile is an alcohol and X is NH for essentially each occurrence of X is shown in Formula (XI):

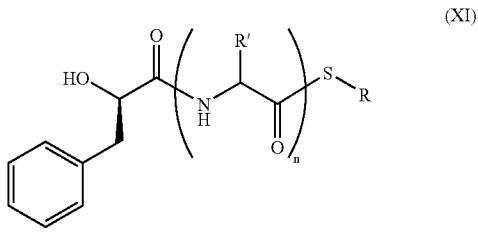

wherein:
n is an integral number greater or equal to 5;
R is as defined in Formula (I); and
each R' is independently chosen for each occurrence for R' in Formula (XI) from the side chain substituents of the synthetic and biosynthetic amino acid side chain residues and each residue can have either D or L stereoconfiguration.

Preferably, the substrate is sufficiently polar such that its solubility and that of the resulting macrocyclic molecule in the aqueous reaction medium is at least 0.1 g/L, preferably at least 1 g/L, and more preferably at least 10 g/L.

Preferred R groups in Formula (XI) are optionally substituted N-$C_2$-$C_6$alkanoyl$C_2$-$C_6$aminoalkyl. More preferably, the R group is a N-acetyl$C_2$-$C_6$aminoalkyl and a particularly preferred R group is N-acetylaminoethyl (e.g., SR together is N-acetylcysteamine, SNAC).

A macrocyclic molecule according to Formula (XII) is prepared by excised TE domain protein catalyzed cyclization of substrates according to formula (XI).

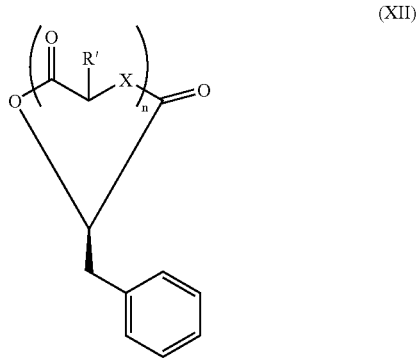

wherein:
R' and n are defined as in Formula (XI).

Substrates according to Formula (XI) generate macrolactone molecules according to Formula (XII) upon cyclization. Similarly, macrolactone molecules according to Formula (VIII) can also be generated from substrates that include ester linkages according to Formula (VII) where the nucleophile, Nuc, is $NH_2$ and at least one occurrence of X is an O atom. A number of important biologically active molecules comprise macrolactone structures including surfactin, fengycin, calcium-dependent antibiotic (CDA), epothiolone, daptomycin, syringomycin, nystatin, lichenysin, erythromycin and the like.

Substrates useful in the practice of the present invention further include substrate molecules according to Formula (I) wherein the linker optionally comprises one or more amino acid residues and at least one non-peptidic spacer as shown in Formula (XIII):

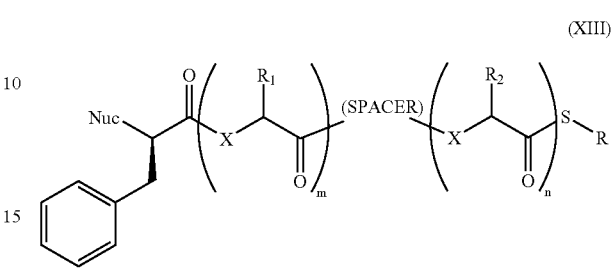

wherein:
R is defined as in Formula (I);
$R_1$ and $R_2$ are defined as in Formula (V);
Nuc is chosen from $NH_2$ or OH;
X is independently chosen from O or NH for each occurrence of X;
m and n are independently chosen non-negative integers that can be the same or different;
SPACER is a group of atoms or functional group residues that are not amino acid residues or depsipeptide residues that comprise z atoms in the linear backbone of the substrate;
z is greater than or equal to 2; and
the sum of z+3m+3n is greater or equal to 12.

Preferably, the substrate is sufficiently polar such that its solubility and that of the resulting macrocyclic molecule in the aqueous reaction medium is at least 0.1 g/L, preferably at least 1 g/L, and more preferably at least 10 g/L.

Formula (XIII) depicts a substrate with one synthetic, non-peptidic spacer. However, substrates that contain two, three or more non-peptidic spacers interspersed among peptide or depsipeptide sequences that meet the requirements outlined in Formula (XIII) are also substrates of the present invention.

Preferable non-peptidic spacers according to Formula (XIII) comprise at least 2 atoms in the substrate backbone. More preferable are spacers with 6 to 12 atoms in the substrate backbone.

Preferred non-peptidic spacers of the present invention comprise one or a combination of more than one of the following optionally substituted groups that include $C_1$-$C_{12}$-alkyl, $C_2$-$C_{12}$-alkenyl, $C_2$-$C_{12}$-alkynyl, $C_3$-$C_7$-cycloalkyl, $C_3$-$C_7$-heteroalicyclic, aryl, heteroaryl, amine (NH), $C_1$-$C_{12}$-alkylamino, amide, ester, ketone, sulfoxide, ether, thioether, imine, sulfone, and the like. More preferable are spacers that comprise one or a combination of more than one of the following optionally substituted groups that include α,ω-alkandiyl, α,ω-alkane diol, α,ω-alkane diamine, ω-(1-alkanol)amine, ω-hydroxyalkanoate or ω-aminoalkanoate functional groups linked together by independently chosen ether, amine, amide or ester bonds.

Particularly preferred non-peptidic spacers of the present invention include one or a combination of more than one of the following optionally substituted groups glycine, glycolate, O-(2-aminoethyl)glycolate, O-(2-ethanol)glycolate, O-(2-(2-aminoethoxy)ethyl)glycolate, O-(diethylene glycol) glycolate, and the like that are linked together by either amide or ester bonds.

A macrocyclic molecule according to Formula (XIV) is prepared by excised TE domain protein catalyzed cyclization of substrates according to formula (XIII).

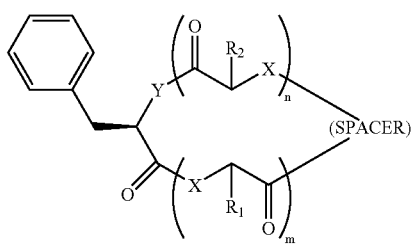

(XIV)

wherein:

m, n, z, SPACER, X, $R_1$ and $R_2$ are defined as in Formula (XIII); and

Y is chosen from O or NH.

The invention further includes methods for the preparation of macrocyclic molecules from substrates that have backbones that are insufficiently long to undergo the macrocyclization methods described above. Macrocyclization methods are disclosed for short substrates that can not be cyclized by excised TE domain protein. The substrate is first dimerized or oligomerized by excised TE domain protein in one or more elongation steps until the substrate dimer or oligomer has sufficient length to undergo macrocyclization catalyzed by the excised TE domain protein. The dimerization or oligomerization process catalyzed by the excised TE domain protein can generate homo- or hetero-dimers or oligomers by choosing to ligate two identical substrates or two different substrates. The elongation-macrocyclization method comprises elongating a substrate molecule that essentially can not be cyclized by an excised TE domain protein. The substrate molecule elongation occurs by contacting excised TE domain protein with a first substrate molecule under conditions conductive to formation of a TE-O-acyl substrate intermediate. A nucleophile from a second substrate can intermolecularly displace the TE domain to form an intermediate substrate dimer that comprises a linear backbone that is twice the length of the original substrate. The excised TE domain protein catalyzed elongation of the substrate molecule is repeated until the intermediate substrate oligomer is of sufficient length to undergo macrocyclization catalyzed by excised TE domain protein. Contacting the intermediate substrate dimer or substrate oligomer with excised TE domain protein under conditions conductive to formation of a TE-O-acyl substrate dimer or oligomer intermediate. The intramolecular recognition element nucleophile can displace the TE domain to form the elongated macrocyclic product molecule.

Substrates suitable for use in the cascade elongation-macrocyclization method of the invention catalyzed by excised TE domain protein are depicted in Formula (XV):

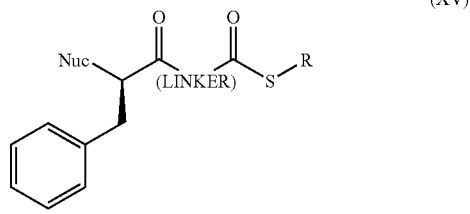

(XV)

wherein:

Nuc and R are defined as in Formula (I);

LINKER is a group of atoms or functional group residues, connecting the thioester and the 2-(Nuc)-3-phenyl-propionyl residues, that comprises a linear backbone of between about 5 and 14 atoms; and R is a lower alkyl group that can be substituted.

Preferably, the substrate is sufficiently polar such that its solubility and that of the resulting macrocyclic molecule in the aqueous reaction medium is at least 0.1 g/L, preferably at least 1 g/L, and more preferably at least 10 g/L.

Preferable R groups are optionally substituted $N-C_2-C_6$alkanoyl$C_2-C_6$aminoalkyl. More preferably, the R group is a N-acetyl$C_2-C_6$aminoalkyl and a particularly preferable R group is N-acetylaminoethyl (e.g. SR is N-acetylcysteamine, SNAC).

In preferred substrates, the linker according to Formula (XV) has between about 8 and 11 atoms in the linear substrate backbone. Additionally, the linker can comprise amino acid residues linked by amide or ester bonds, or synthetic non-peptidic groups such as those groups defined for the spacer in Formula (XIII).

A macrocyclic molecule according to Formula (XVI) is prepared by excised TE domain protein catalyzed cyclization of substrates according to formula (XV).

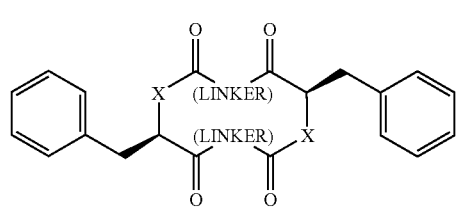

(XVI)

wherein:

LINKER is defined as in Formula (XV); and

X is chosen from S, O and NH.

Additional substrates useful in the practice of the invention are molecules according to Formula (XV) wherein the thioester is attached to a linker such that the C-terminus of the substrate is a dipeptide according to Formula (XVII):

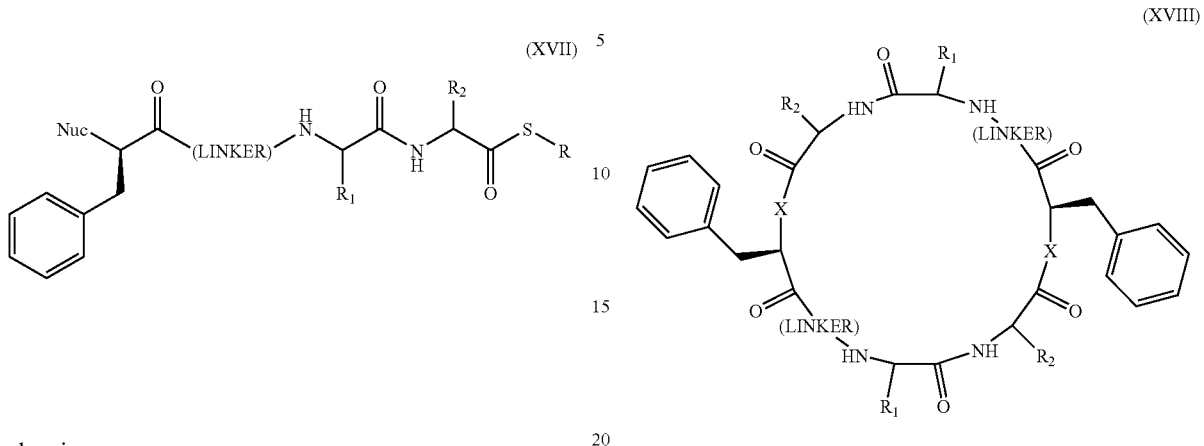

wherein:

Nuc and R are defined as in Formula (I);

LINKER is a group of atoms or functional group residues, connecting the thioester and the 2-(Nuc)-3-phenyl-propionyl residues, that comprises a linear backbone of between about 3 and 9 atoms; and $R_1$ and $R_2$ are chosen from the side chain substituents of the synthetic and biosynthetic amino acid side chain residues and each residue can have either D or L stereoconfiguration. $R^1$ and $R_2$ are chosen independently and can be the same or different.

Preferably, the substrate is sufficiently polar such that its solubility and that of the resulting macrocyclic molecule in the aqueous reaction medium is at least 0.1 g/L, preferably at least 1 g/L, and more preferably at least 10 g/L.

In preferred embodiments, a substrate according to Formula (XVII) further comprises a dipeptide in which $R_1$ comprises a group that is charged at pH 7. Preferably, $R_1$ is an optionally substituted ω-amino-$C_1$-$C_6$alkyl or a charged side chain from a biosynthetic amino acid. Particularly preferred are substrates where $R_1$ is the side chain from ornithine.

Also preferable are substrates according to Formula (XVII) where $R_2$ is an optionally substituted $C_1$-$C_6$alkyl group. More preferably $R_2$ is a linear or branched $C_1$-$C_6$alkyl group.

Preferable R groups in Formula (XVII) are optionally substituted N-$C_2$-$C_6$alkanoyl$C_2$-$C_6$aminoalkyl. More preferably, the R group is a N-acetyl$C_2$-$C_6$aminoalkyl and a particularly preferable R group is N-acetylaminoethyl (e.g. SR is N-acetylcysteamine, SNAC).

In preferred substrates, the linker according to Formula (XVII) has between about 6 and 9 atoms in the linear substrate backbone. Additionally, the linker can comprise amino acid residues linked by amide or ester bonds, or synthetic non-peptidic groups such as those groups defined for the spacer in Formula (XIII).

A macrocyclic molecule according to Formula (XVIII) is prepared by excised TE domain protein catalyzed cyclization of substrates according to formula (XVII).

wherein:

LINKER, $R_1$ and $R_2$ are defined as in Formula (XVII); and

X is chosen from S, O and NH.

In other preferred embodiments of the present invention, other macrocyclization substrates that may not meet the requirements of Formulas (I), (V), (VII), (IX), (XI), (XIII), (XV) and (XVII) that can be cyclized by excised TE domain proteins other than the excised TE domain protein from tyrocidine synthetase are also suitable substrates of the invention. The substrates set forth in Formulas (I), (V), (VII), (IX), (XI), (XIII), (XV) and (XVII) have significant similarity near the N- and C-termini to the wild-type substrate having the sequence of tyrocidine A (i.e. D-Phe-Pro-Phe-D-Phe-Asn-Gln-Tyr-Val-Orn-Leu-SNAC). An appropriate excised TE domain protein capable of catalyzing the macrocyclization of a specified substrate to a macrocyclic molecule can be accomplished by comparison of the groups near the parts of the specified substrate to be joined by the macrocyclization reaction with the corresponding groups of wild-type substrates of a family of TE domain proteins. Preferred TE domain proteins are those whose wild-type substrate has the highest degree of similarity with the specified substrate.

In additional preferred embodiments of the invention, macrocyclic molecules prepared by the methods of the present invention can have useful pharmaceutical applications that include but are not limited to use as antibiotics, antitumor agents, cholesterol-lowering drugs, and immunosuppressants. Other applications and molecules with other biological activity profiles are also suitable for the present invention.

All publications disclosed herein are incorporated herein by reference. The following non-limiting examples are illustrative further of the invention.

EXAMPLE 1

Preparation of Peptide Substrates

Peptides were prepared by automated solid-phase synthesis (0.3 mmol scale, diisopropylcarbodiimide (DIPCDI)/hydroxybenzotriazole (HOBt) activation) on 2-chlorotrityl resin derivatized with the appropriate C-terminal amino acid using Fmoc-protected monomers (side chain protecting groups used were trityl for Asn and Gln, t-butyl for Tyr, and Boc for Orn) except for the N-terminal monomer, which was Boc-protected. The peptide was cleaved from the resin using 1:1:3 acetic acid/trifluoroethanol/dichloromethane (DCM) (3 hours, 24° C.), then precipitated with n-hexane and the solvent removed by rotary evaporation. The protected peptide (1 eq.) was dissolved in tetrahydrofuran (THF) or dimethylformamide (DMF). A solution of dicylcohexylcarbodiimide (DCC) (1.2 eq.) and HOBt (1.2 eq.) in THF (or DMF) and N-acetylcysteamine (2.5 eq.) were added, and the reaction stirred for 35 minutes at 24° C. Potassium carbonate (0.6 eq.) was then added and the reaction stirred for 3 hours at 24° C., filtered and concentrated. The protected peptide-SNAC was treated with 16:3:1 trifluoracetic acid (TFA)/DCM/N-acetylcysteamine (3 hours, 24° C.) and precipitated with ether. Reverse-phase ($C_{18}$) HPLC purification (20 to 50% acetonitrile in 0.1% TFA/water over 30 minutes) afforded the peptide-SNAC TFA salt (10-25% yield from the protected peptide) in >95% purity (by analytical HPLC) as a white solid. The identities of all the peptide-SNACs were verified by MALDI-TOF mass spectrometry.

EXAMPLE 2

Substrate Macrocyclization

Macrocyclization reactions were carried out in 25 mM MOPS, pH 7.0 in a total volume of 400 μL. Reactions were initiated by addition of TycC TE and quenched at various time points by the addition of 25 μL 1.7% TFA/water, flash frozen in liquid nitrogen and stored at −80° C. (for Ex. 13, reactions were quenched by the addition of sodium phosphate, pH 5.3, to 100 mM). The reactions were then thawed, 85 μL acetonitrile added, and analyzed by analytical HPLC with monitoring at 220 nm (20% to 80% acetonitrile in 0.1% TFA/water, or in 25 mM potassium phosphate, pH 5.3 for Ex. 13, over 35 minutes, Vydac protein and peptide $C_{18}$ column). Initial rates were calculated using 1 minute time points. Peptide-SNAC and reaction product concentrations were determined for all Tyr-containing peptides based on the estimated extinction coefficient ε (280 nm)=1,280 $M^{-1}$ $cm^{-1}$, which agrees with the experimentally determined ε (280 nm) of Ex. 1. For peptide-SNACs not containing Tyr, ε (220 nm) was determined experimentally, and concentrations of corresponding cyclic products determined by assuming equal ε (220 nm) values for the peptide-SNAC and cyclic product.

EXAMPLE 3

Formation of Tyrocidine A

Figure 2:
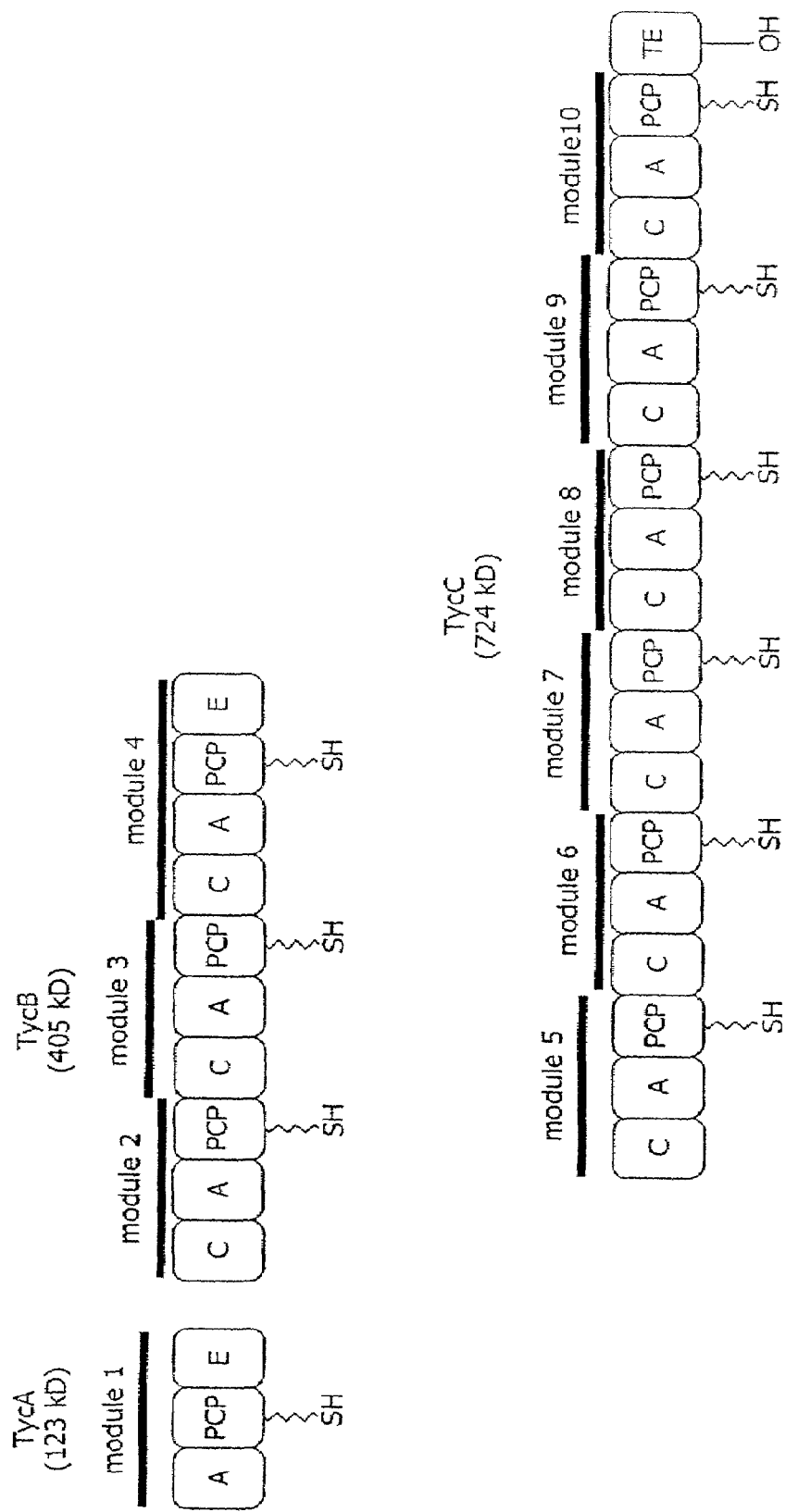
FIG. 2(a) is an illustration of the tyrocidine non-ribosomal peptide synthetase from *Bacillus Brevis*.
FIG. 2(b) is a systematic illustration of the reaction scheme for the macrocyclization catalyzed by the TE domain from tyrocidine synthetase in the natural context of the intact NRPS protein (TycC).
FIG. 2(c) is a systematic illustration of the reaction scheme for the formation of tyrocidine A according to the methods of the present invention.
FIG. 2(d) is a HPLC analysis of the reaction products of a macrocyclization reaction to form tyrocidine A.
Figure 2:
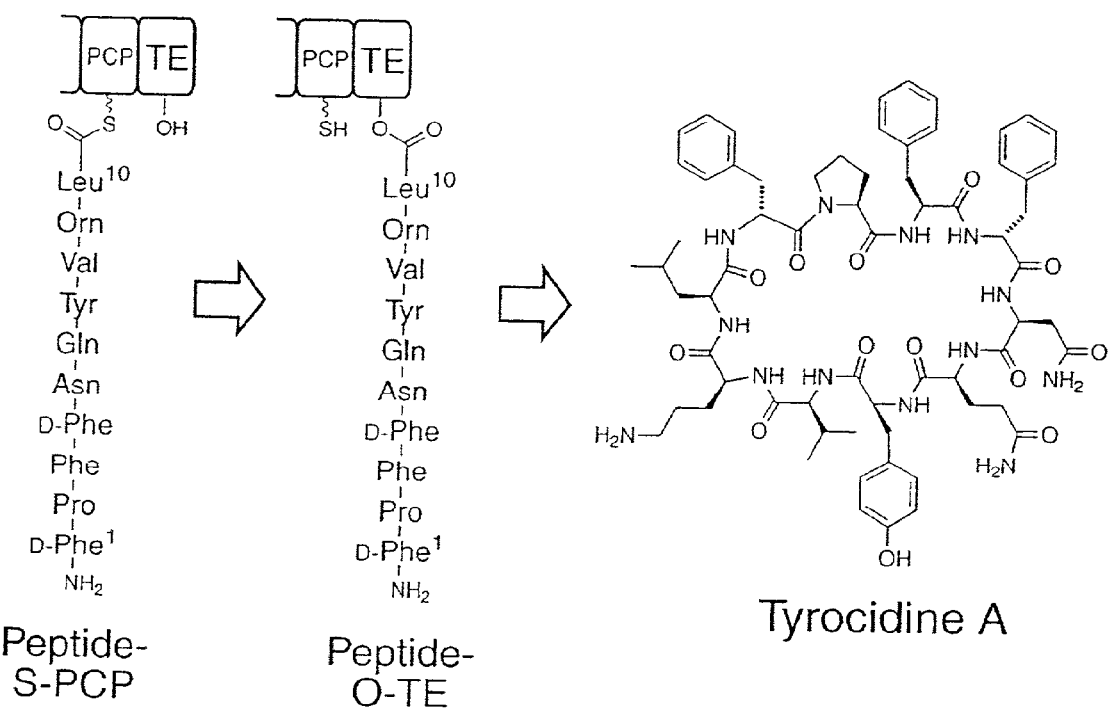
Figure 2:
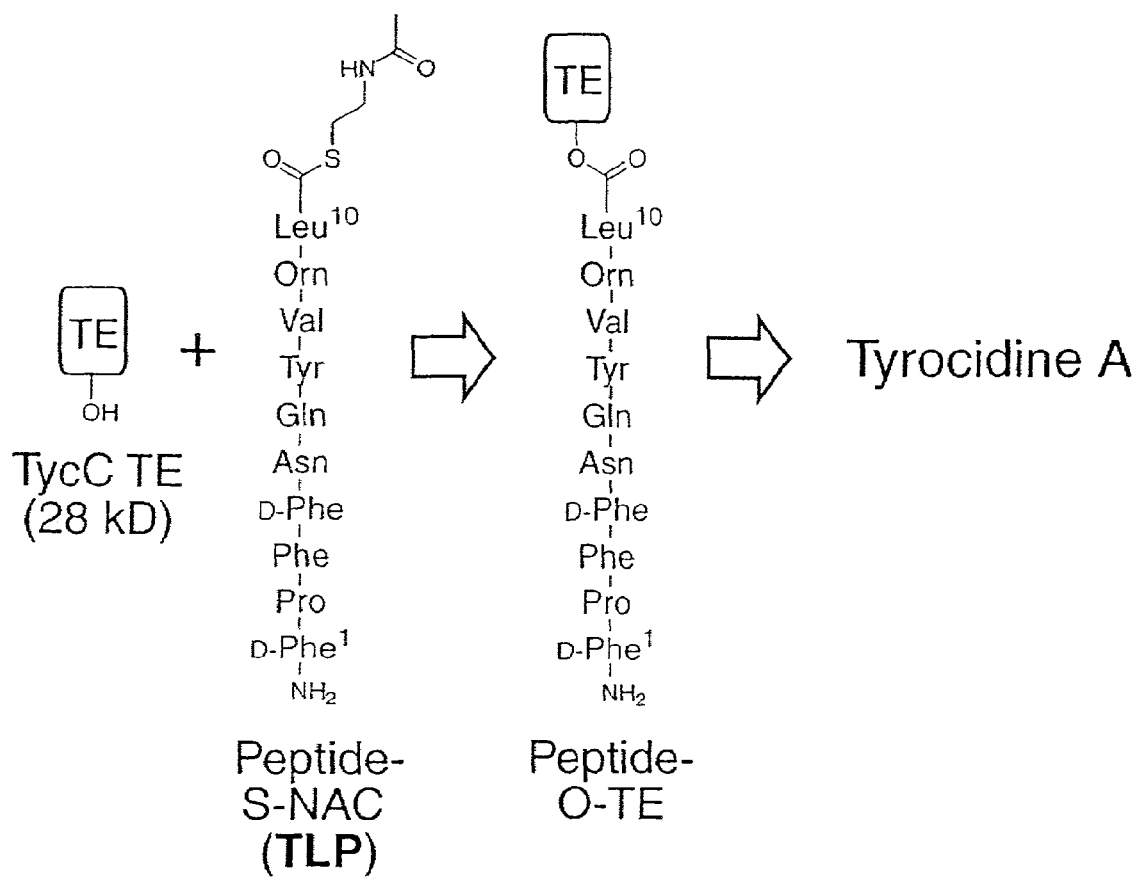
Figure 2:
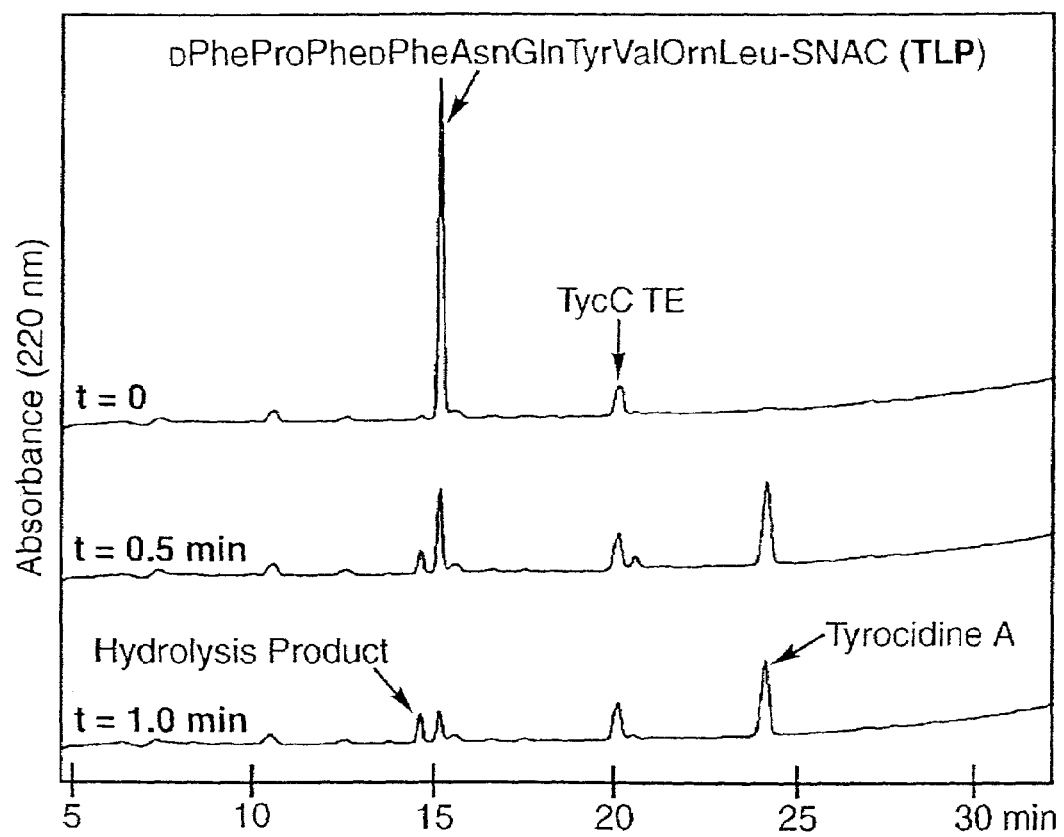

When the decapeptide-SNAC corresponding to the tyrocidine A sequence (D-Phe-Pro-Phe-D-Phe-Asn-Gln-Tyr-Val-Orn-Leu-SNAC, Example 3) (Orn=ornithine) was incubated with purified TycC TE, efficient cyclization to tyrocidine A as well as a minor flux of hydrolysis to the decapeptide was observed (ratio of cyclization:hydrolysis=6:1) (FIG. 2A). The cyclic product was identified as tyrocidine A by HPLC co-elution with authentic tyrocidine A and by mass spectrometry. Kinetic analysis of the cyclization reaction established a $k_{cat}$ of 59 turnovers per minute and a $K_M$ of 3 μM. No hydrolysis or cyclization is detectable under the reaction conditions in the absence of enzyme.

EXAMPLES 4-17

Substrate peptide-SNACs for Examples 4-17 were prepared similarly to the peptide-SNAC for Example 3.

TABLE 1

Kinetic parameters for macrocyclization of various peptide-SNAC substrates to form tyrocidine A (Ex. 3) and related macrocyclic peptides (SNAC = N-acetylcysteamine).

| Example | Residue | $k_{cat}$ | $K_M$ |
|---|---|---|---|
| 3 | D-Phe-Pro-Phe-D-Phe-Asn-Gln-Tyr-Val-Orn-Leu-SNAC | 59 | 3 |
| 4 | Phe-Pro-Phe-D-Phe-Asn-Gln-Tyr-Val-Orn-Leu-SNAC | 0 | — |
| 5 | D-Ala-Pro-Phe-D-Phe-Asn-Gln-Tyr-Val-Orn-Leu-SNAC | 0 | — |
| 6 | D-Phe-Ala-Phe-D-Phe-Asn-Gln-Tyr-Val-Orn-Leu-SNAC | ~55 | 3 |
| 7 | D-Phe-Pro-Ala-D-Phe-Asn-Gln-Tyr-Val-Orn-Leu-SNAC | 50 | 6 |
| 8 | D-Phe-Pro-Phe-D-Ala-Asn-Gln-Tyr-Val-Orn-Leu-SNAC | 105 | 6 |
| 9 | D-Phe-Pro-Phe-D-Phe-Ala-Gln-Tyr-Val-Orn-Leu-SNAC | ~30 | 6 |
| 10 | D-Phe-Pro-Phe-D-Phe-Asn-Ala-Tyr-Val-Orn-Leu-SNAC | ~35 | 4 |
| 11 | D-Phe-Pro-Phe-D-Phe-Asn-Gln-Ala-Val-Orn-Leu-SNAC | ~45 | 15 |
| 12 | D-Phe-Pro-Phe-D-Phe-Asn-Gln-Tyr-Ala-Orn-Leu-SNAC | 50 | 9 |
| 13 | D-Phe-Pro-Phe-D-Phe-Asn-Gln-Tyr-Val-Glu-Leu-SNAC | 0.6 | 56 |
| 14 | D-Phe-Pro-Phe-D-Phe-Asn-Gln-Tyr-Val-Orn-Ala-SNAC | ~16 | 6 |
| 15 | D-Phe-Pro-Phe-Asn-Gln-Tyr-Val-Orn-Leu-SNAC | ~5 | 6 |
| 16 | D-Phe-Pro-Phe-D-Phe-Asn-Ala-Gln-Tyr-Val-Orn-Leu-SNAC | ~48 | 20 |
| 17 | D-Phe-Pro-Val-Orn-Leu-D-Phe-Pro-Val-Orn-Leu-SNAC | 12 | 5 |

All cyclic products were characterized by MALDI-TOF mass spectrometry. Cyclic products enzymatically synthesized from Examples 3, 6, 14, 15, 16, and 17 were further characterized by ESI-ion trap mass spectrometry. Enzymatically synthesized (Ex. 3) and authentic tyrocidine A gave identical fragment ions, including four internal fragment ions (observed both with and without loss of $NH_3$ from Asn or Gln) that contain the Leu10-D-Phe1 dipeptide segment formed by head-to-tail cyclization, and at least two of the corresponding fragment ions were identified for cyclic peptides from Examples 6, 14, 15 and 16, confirming that these products result from head-to-tail cyclization. For example, an Orn9 to Tyr7 ion was observed for each macrocyclic molecule product, the observed amino acid sequence is referred to by their shortened one letter description (Ex. 3, M+H calc'd for OLFPFFNQY: 1157.6, observed 1157.6; Ex. 6, M+H calc'd for OLFAFFNQY: 1131.6, observed: 1131.5; Ex. 14, M+H calc'd for OAFPFFNQY: 1115.5, observed: 1115.5; Ex. 15, M+H calc'd for OLFPFNQY: 1009.5, observed 1009.3 Ex. 16, M+H calc'd for OLFPFFNAQY: 1228.6, observed: 1228.6). Similarly, the Ex. 17 macrocyclic molecule product and authentic gramicidin S gave the same fragmentation pattern, and one ion confirming head-to-tail cyclization was detected in both samples (Ex. 17, M+H calc'd for LFPVOLFPV: 914.6, observed 914.5).

A systematic representation of a TE-catalyzed cyclization reaction in the natural context of an intact NRPS or PKS multidomain protein is depicted in FIG. 1(a). Each box represents a functional protein domain: A, adenylation domain; CP, carrier protein domain (either aryl carrier protein domain, acyl carrier protein domain, or peptidyl carrier protein domain); TE, thiesterase domain. Thiol (SH) and hydroxyl (OH) groups represent phosphophantetheine and the TE active site serine residue, respectively. Nuc represents a nucleophilic group, which is usually $NH_2$ (amine) or OH (hydroxyl), and x represents the nucleophilic group after the reaction (usually NH or O). The tyrocidine non-ribosomal peptide synthetase from *Bacillus brevis* is illustrated in FIG. 2(a). Synthetase subunits TycA, TycB and TycC are represented by a series of boxes where each box represents a functional domain: A, adenylation domain (catalyzes amino acid activation); PCP, peptidyl carrier protein domain; C, condensation domain (catalyzes peptide bond formation); E, epimerization domain; TE, thioesterase domain.

A systematic representation of the present invention is depicted in FIG. 1(b), which comprises: contacting purified excised TE domain protein with a substrate that comprises an activated acyl residue and a pendant nucleophile separated by a linear backbone under conditions conductive to formation of a TE-O-acyl bond such that the pendant intramolecular nucleophile can displace the TE domain to form the macrocyclic product. R' represents an alkyl group that may be substituted.

A systematic representation of the macrocyclization reaction catalyzed by the TE domain from tyrocidine synthetase in the natural context of the intact NRPS protein (TycC) is depicted in FIG. 2(b). A non-limiting example of the macrocyclization method of the present invention is depicted in FIG. 2(c). The macrocyization of decapeptide thioester (TLP, Ex. 3) catalyzed by the excised TE domain protein from the tyrocidine NRPS (TycC TE) to form the cyclic peptide antibiotic tyrocidine A is illustrated. A HPLC analysis is presented in FIG. 2(d) of the reactions that initially contained 2 µM TLP, 50 nM TycC TE and 25 mM MOPS (pH 7.0, 24° C.) with reaction times of 0, 0.5 and 1 minute.

The present inventors have further discovered the macrocyclization method catalyzed by excised TE domain will cyclize substrates that differ from the wild-type tyrocidine A sequence. Specifically, the N-terminal residue D-Phe1 was replaced with L-Phe1 (Ex. 4) or D-Ala (Ex. 5), D-Phe4 with D-Ala (Ex. 8), Orn9 with Glu (Ex. 13), and each of the other seven residues with Ala. Kinetic parameters were determined for cyclization for each of the mutant substrates. Mutation of the N-terminal residue D-Phe1 to either L-Phe (Ex. 4) or D-Ala (Ex. 5) arrests cyclization activity, indicating that recognition of both stereochemistry and side chain identity of this residue is essential for cyclization. Thioester hydrolysis is observed in Examples 4 and 5, with kinetic parameters similar to the wild-type substrate (Ex. 3) indicating that these mutations affect the cyclization step and not peptide-O-TE formation.

Preferred macrocyclization substrates of the present invention comprise at least one charged group. Particularly preferred are substrates that comprise at least one ornithine (Orn) residue. Recognition of Orn9 is also important for cyclization: when changed to Glu (Ex. 13), cyclization still occurs, but with $k_{cat}$ decreased by 100-fold and $K_M$ increased by 20-fold. Changing Orn to Glu affects cyclization and hydrolysis equally, indicating that the mutation affects the peptide-O-TE formation step. Any charged functionality or residue for which substrate cyclization occurs and maintains substrate solubility in water is acceptable.

Mutants in which each of the remaining eight residues are changed to alanine (without changing the D or L configuration) have relatively little effect on cyclization kinetics: $k_{cat}$ values for all of these substrates are within a factor of 2 of the wild-type substrate (Ex. 3) except for Example 14 (4-fold reduction in $k_{cat}$), and all of the $K_M$ values are within a factor of 2 of (Ex. 3) except Example 11 (5-fold increase in $K_M$) and Example 12 (3-fold increase in $K_M$). See Table 1.

The macrocyclization method catalyzed by TycC TE domain is effective at cyclizing a variety of substrates according to Formula (VII) that retain the key "recognition residues". The 9-residue (D-Phe-Pro-Phe-Asn-Gln-Tyr-Val-Orn-Leu-SNAC, Ex. 15) and the 11-residue (D-Phe-Pro-Phe-D-Phe-Asn-Ala-Gln-Tyr-Val-Orn-Leu-SNAC, Ex. 16) substrates in which one residue near the center of the wild-type sequence is either deleted or inserted were prepared. Both 9- and 11-membered substrates are cyclized by TycC TE domain. The 14-fold reduction in $k_{cat}$ for Example 15 may result from strain in the cyclic conformation. These results demonstrate that TycC TE can catalyze formation of cyclic peptides with various ring sizes. Additional substrates that range in length from 6 to 14 residues were synthesized and shown to cyclize with kinetic parameters similar to to the wild-type substrate (Ex 18-21). Preferable substrates have at least 6 residues than are incorporated into the macrocyclic ring. Particularly preferred substrates have between about 8 and about 16 amino acid residues or between about 24 and about 48 atoms in the linear backbone that are incorporated into the macrocyclic ring.

TABLE 2

Kinetic parameters for cyclization of various peptide-SNAC substrates to from macrocyclic peptides containing 6 (Ex. 18), 8 (Ex. 19), 12 (Ex. 20) or 14 (Ex. 21) amino acids.

| Example | Sequence | $k_{cat}$ (min$^{-1}$) | $K_M$ (µM) |
|---|---|---|---|
| 18 | D-Phe-Orn-Leu-D-Phe-Orn-Leu-SNAC | 30 | 4 |
| 19 | D-Phe-Pro-Orn-Leu-D-Phe-Pro-Orn-Leu-SNAC | 17 | 3 |
| 20 | D-Phe-Pro-Leu-Val-Orn-Leu-D-Phe-Pro-Leu-Val-Orn-Leu-SNAC | 22 | 6 |

TABLE 2-continued

Kinetic parameters for cyclization of various peptide-SNAC substrates to from macrocyclic peptides containing 6 (Ex. 18), 8 (Ex. 19), 12 (Ex. 20) or 14 (Ex. 21) amino acids.

| Example | Sequence | $k_{cat}$ (min$^{-1}$) | $K_M$ (μM) |
|---|---|---|---|
| 21 | D-Phe-Pro-Val-Leu-Val-Orn-Leu-D-Phe-Pro-Val-Leu-Val-Orn-Leu-SNAC | 6 | 5 |

A systematic representation of the successive pentapeptide dimerization and decapeptide cyclization reactions catalyzed by the TE domain from Gramicidin S synthetase in the natural context of the intact NRPS protein (GrsB) is depicted in FIG. 3(b) and Gramicidin S synthetase from *B. Brevis* is illustrated in FIG. 3(a). The sequence of steps in the reaction are (i) a pentapeptide is built up by the synthetase and transferred to the TE active site serine, (ii) a second pentapeptide is built up, (iii) the N-terminal amine of the pentapeptide-S-PCP reacts with the peptide-O-TE to form a decapeptide-S-PCP intermediate, and (iv) the PCP-tethered decapeptide is transferred to the TE serine and cyclized. A systematic representation of an illustrative example of the elongation/cyclization method of the invention is depicted in FIG 3(c) where a pentapeptide thioester (GLP 5) undergoes dimerization and successive macrocyclization of the resulting decapeptide thioester catalyzed by the excised TE domain protein from the tyrocidine NRPS (TycC TE) to form the cyclic peptide antibiotic gramicidin S. A HPLC analysis of this reaction after one (1) minute is presented in FIG. 3(d) where the reaction initially contained 200 μM GLP5, 100 nM TycC TE and 25 mM MOPS (pH 7.0, 24° C.).

Figure 3:
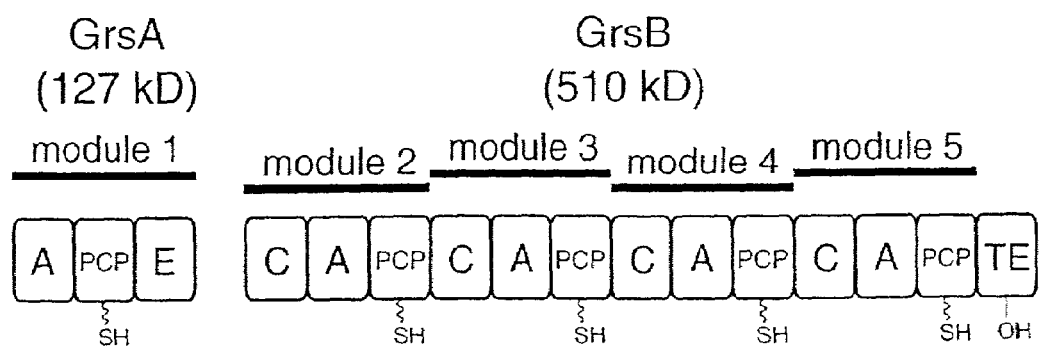
FIG. 3(a) is an illustration of the Gramicidin S synthetase from *B. brevis*.
FIG. 3(b) is a systematic illustration of the reaction scheme for the successive pentapeptide dimerization and decapeptide cyclization catalyzed by the TE domain from Gramicidin S synthetase in the natural context of the intact NRPS protein (GrsB).
FIG. 3(c) is a schematic illustration of the formation of gramicidin S according to the elongation macrocyclization method of the present invention.
FIG. 3(d) is a HPLC analysis trace of the reaction products from an elongation macrocyclization cyclization reaction to form gramicidin S.
Figure 3:
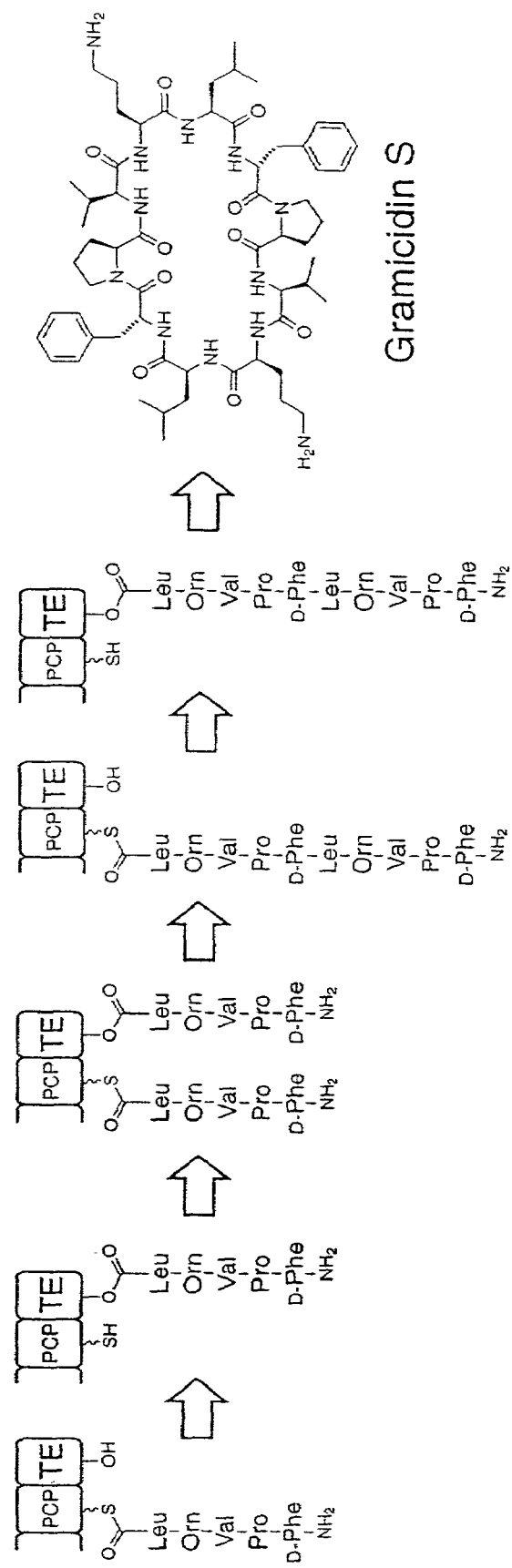
Figure 3:
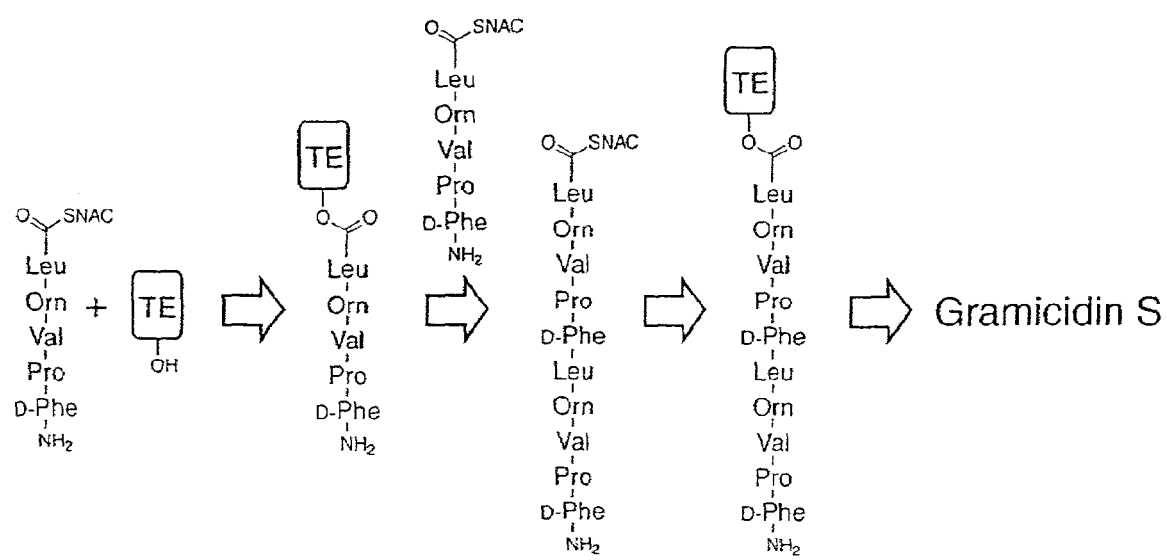
Figure 3:
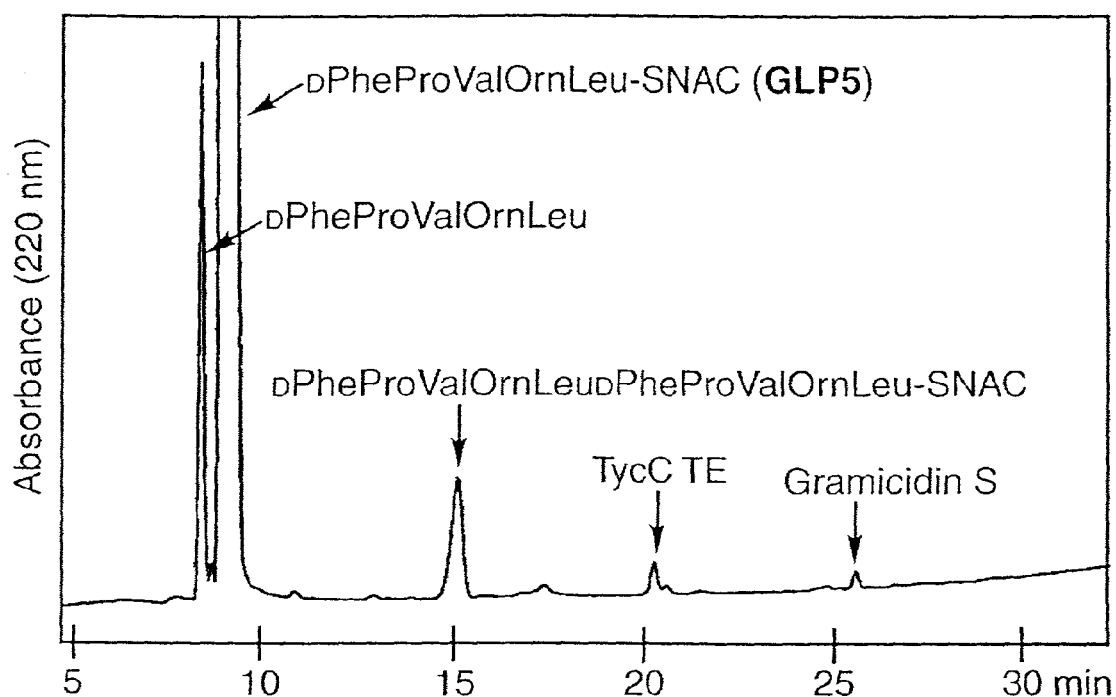

Also, in accordance with the present invention, a method for preparing macrocyclic molecules by sequential chain elongation (ligation) and cyclization catalyzed by excised TE domain was discovered. The cyclic decapeptide antibiotic gramicidin S has an amino acid sequence with a pentapeptide repeat (D-Phe-Pro-Val-Orn-Leu) that includes the same two N-terminal residues (D-Phe-Pro) and the same three C-terminal residues (Val-Orn-Leu) as the tyrocidine A substrate sequence. These common N- and C-terminal sequences are sufficient for substrate recognition. The TycC TE domain is able to catalyze the dimerization of pentapeptide-SNAC (D-Phe-Pro-Val-Orn-Leu-SNAC, Example 17) to form a decapeptide-SNAC that undergoes TE domain catalyzed macrocyclization to gramicidin S (FIG. 4). Upon incubation of pentapeptide-SNAC with TycC TE, efficient chain dimerization and subsequent cyclization occurred as well as substrate hydrolysis to the pentapeptide. The identities of the products were confirmed by HPLC co-elution with authentic standards and by mass spectrometry. The mechanisms for gramicidin S preparation by either the gramicidin S NRPS system and by TycC TE catalyzed elongation/cyclization method are depicted in FIG. 3. The ligation (Jackson *Science* (1994) 266:243-7) and cyclization of synthetic acyl-thioesters is a generally useful application of excised TE domains from PKS and NRPS systems for the preparation of symmetric cyclic products such as the non-limiting example of thiocoraline, an antitumor antibiotic.

The macrocyclization method of the invention is also capable of cyclizing peptide-thioester substrates wherein one or more of the amide linkages between residues has been replaced with ester linkages. Preferred depsipeptide-thioester substrates include those abovementioned in Formula (VII) wherein one or more occurrence of X is an O atom. A non-limiting example of such a substrate is compound 22, an analog of Example 3, wherein there is an ester linkage between residues Phe3 and D-Phe4, and compound 23, an analog of Example 3, wherein there is an ester linkage between residues Tyr7 and Val8. Cyclization rates for TE domain catalyzed macrocyclization of compounds 22 and 23 are similar to the rate observed for the substrate in Example 3 which has the wild-type tyrocidine A sequence (data not shown). Other preferred substrates include those abovementioned in Formula (VII) where Nuc is a hydroxyl group (Nuc=OH). A non-limiting example of such a substrate is compound 24, an analog of Example 3. Compound 24 is macrocyclized by the excised TE domain protein from tyrocidine synthetase (data not shown).

(22)

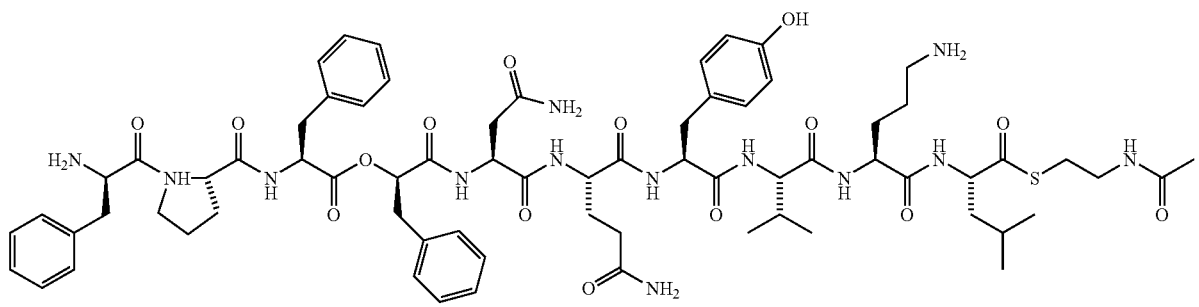

(23)

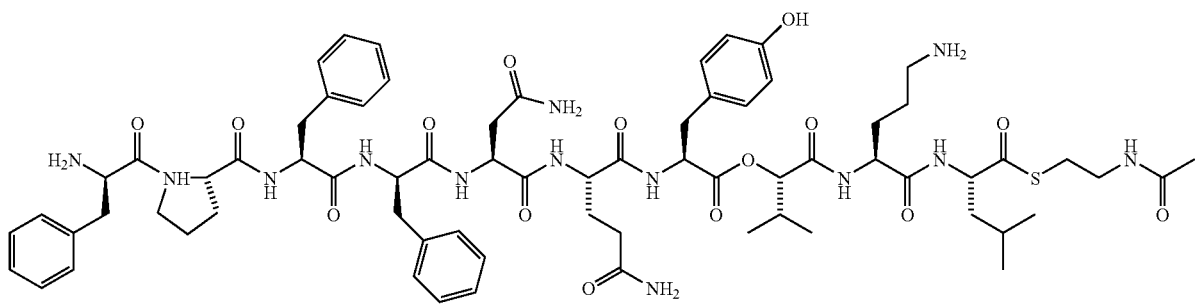

(24)

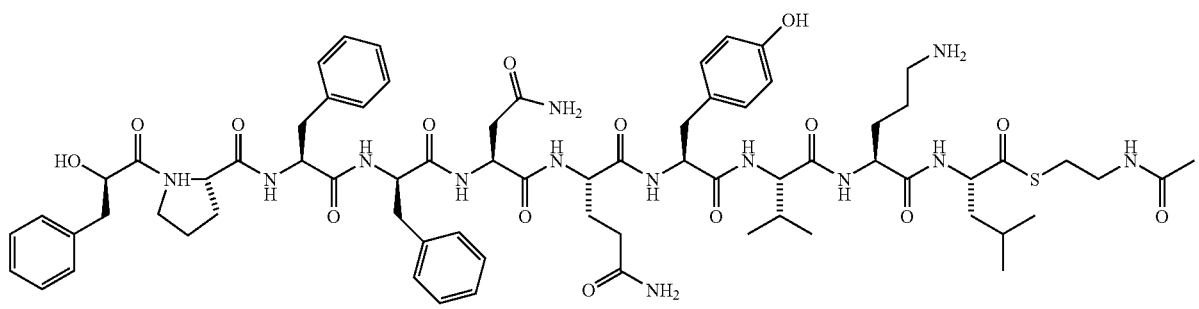

In other specific embodiments of the invention, one or more substrate non-recognition element amino acid residues can be replaced with a non-peptidic linker or a non-peptidic linker can be inserted into a specific point in a chosen peptide sequence such that these substrates remain viable for the TE domain catalyzed cyclization method of the present invention. Substrates comprising a non-peptidic linker have sufficient amino acid residues and main-chain linker atoms to generate a macrocyclic molecule with at least 15 atoms in the macrocyclic ring. In non-limiting examples, 3 or 6 residues of the wild-type peptide-thioester substrate for the excised TE domain from tyrocidine synthetase (Example 3) were replaced with O-(2-(2-aminoethoxy)ethyl)glycolate (25) or the dimer thereof(26). Substrates 25 and 26 are cyclized by the TE domain from tyrocidine synthetase to form 30-member macrocyclic compounds (Data not shown).

(25)

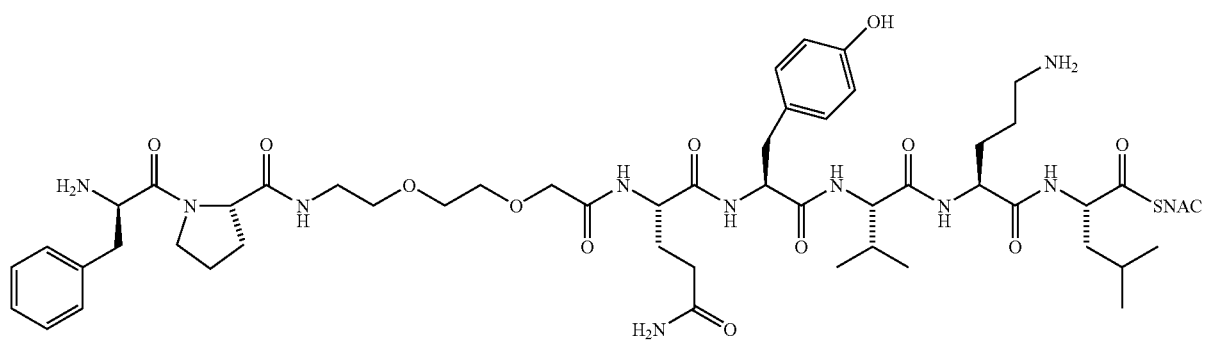

(26)

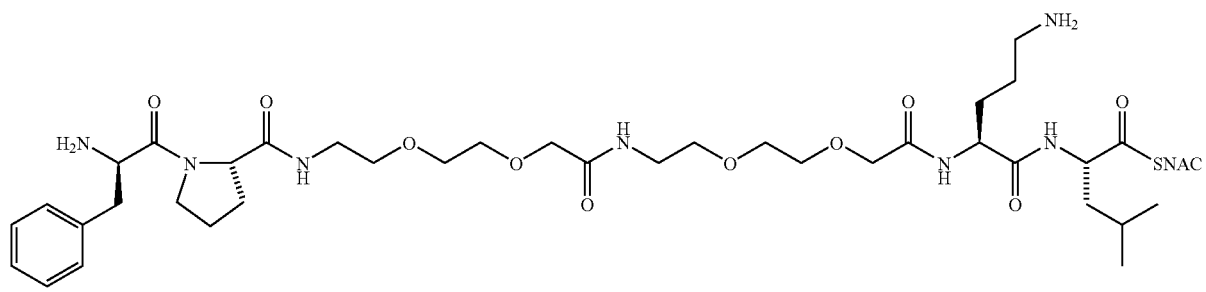

The structural variability of macrocyclization substrates that are cyclized by the TycC TE domain demonstrates the broad substrate specificity exhibited by the method of the present invention. Replacement of non-recognition residues or inserting or deleting residues from the wild-type substrate has little effect on cyclization activity. An illustrative example of the broad substrate specificity of the methods in the present invention is the cyclization of the decapeptide-SNAC intermediate in the synthesis of gramicidin S. The gramicidin S decapeptide-SNAC intermediate (Ex. 17) differed by the substitution of 5 residues (50% of the residues) from the wild-type peptide-SNAC (Ex. 3) and yet the cyclization activity of the two substrates is remarkably similar (5-fold lower $k_{cat}$ and comparable $K_M$ for Ex. 17 as compared to Ex. 3). Thioester substrates comprising non-natural amino acids and amino acids with D-stereochemical configurations can also undergo macrocyclization using the methodology of the present invention wherein these substrates comprise the required recognition elements.

In accord with the present invention, other linear substrate molecules can be cyclized by other excised TE domain proteins besides the TE domain protein excised from the tyrocidine NRPS. In one illustrative example, a heptapeptide thioester substrate molecule (27) with a (R)-3-hydroxybutanamide group attached to its N-terminus is efficiently cyclized to macrolactone (28) by the excised TE domain protein from the surfactin synthetase protein system. The excised surfactin TE domain protein selectively cyclizes substrates with the (R)-hydroxybutanamide nucleophile versus substrates with the (S)-hydroxybutamide nucleophile.

(27)

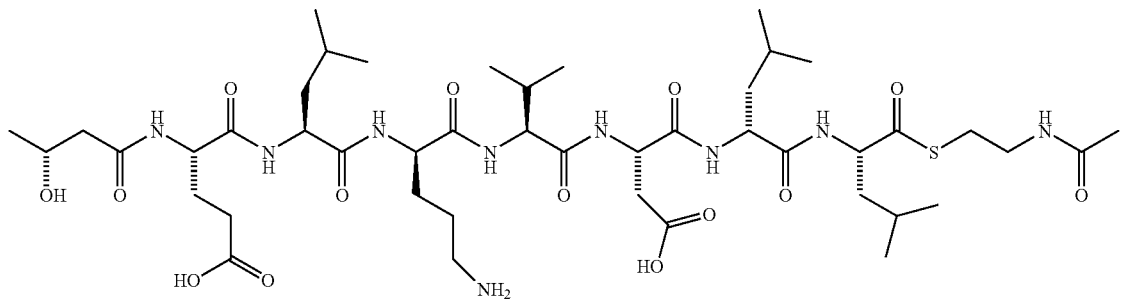

(28)

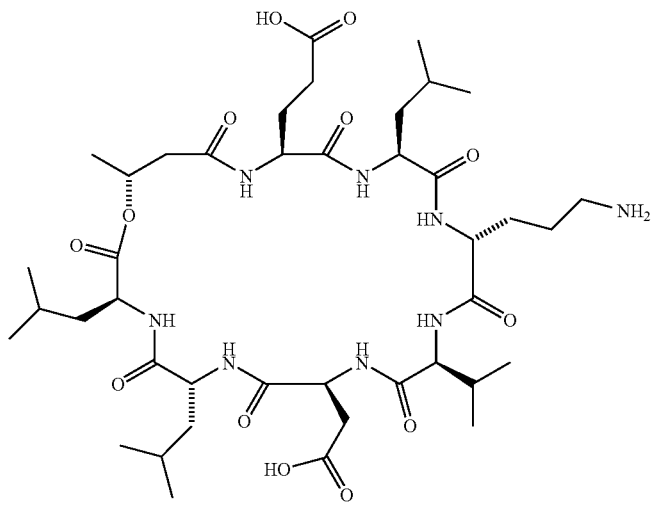

The observed specificity of the surfactin TE domain supports that TE domains can cyclize a variety of substrates provided that certain key recognition elements that are generally near the parts of the molecule that are joined in the cyclization reaction are present. For example, substrate 27 contains a change in the sequence of the heptapeptide compared to the wild-type surfactin sequence (D-Leu3 is changed to D-Orn), but this substrate is nevertheless cyclized by the excised TE domain from surfactin synthetase. When the (R)-hydroxybutanamide nucleophile in compound 27 was changed to a (S)-hydroxybutanamide nucleophile (a change near the parts of the molecule joined by the cylization reaction), cyclization activity was abolished.

EXAMPLE 29

Synthesis of Pantebead Resin and Subsequent Solid Phase Peptide Synthesis.

Synthesis of the Pantebead resin begins with polyethylene glycol acrylamide (PEGA) resin (Renil M, Meldal M, et al., *J. Peptide Sci.*, 1998, 4, 195-210) terminating in a free amine moiety. Solid phase peptide coupling of monomethyl suberic acid to the resin was performed by preincubating the acid (5 eq) with HBTU (O-benzotriazol-1-yl-N, N, N',N'-tetramethyluronium hexafluorophosphate) (4.9 eq), HOBt (1-hydroxybenzotriazole hydrate) (5 eq.), and DIEA (diisopropylethylamine) (10 eq.) in DMF for 10 minutes followed by addition to the resin and agitation for 2 hours. The resin was washed 5× with DMF. The above coupling step was repeated a second time with agitation overnight.

The terminal methyl ester was deprotected to the free acid with THF/MeOH/10N NaOH (3/1.5/0.5) and agitation for 30 minutes, followed by acidification by MeOH/2N HCl (5/1) followed by a wash 2× with water and 2× with MeOH. This deprotection step was repeated a second time, and the resin was washed 2× with MeOH, 2× with water, 2× with MeOH, and 3× with DMF. This yields substance 1A.

Coupling of beta-alanine methyl ester hydrochloride was carried out with preincubation of the resin with HBTU (4.9 eq), HOBt (5 eq), and DIEA (10 eq) in DMF for 10 minutes followed by addition of beta-alanine methyl ester hydrochloride (5 eq.) and agitation for 2 hours. The resin was washed 3× with DMF and the coupling step repeated exactly a second time.

Deprotection of the terminal methyl ester was performed exactly as the previous methyl ester deprotection. This yields substance 2A. Coupling of ethanolamine was carried out with preincubation of the resin with HBTU (4.9 eq), HOBt (5 eq), and DIEA (10 eq) in DMF for 10 minutes followed by addition of ethanolamine hydrochloride (20 eq.) and agitation for 2 hours. The resin was washed 3× with DMF, 2× with MeOH, and 3× with DMF. A second coupling was performed with a different coupling reagent. Ethanolamine hydrochloride (20 eq), PyBOP (benzotriazole-1-yloxy-tris-pyrrolidino-phosphonium hexafluorophosphate) (4.9 eq), HOBt (5 eq), and DIEA (10 eq) were all added to the resin in DMF and agitated overnight. The resin was then washed 2× with DMF, 2× with dichloromethane, 2× with MeOH, 2× with water, 2× with MeOH, 2× with dichloromethane, 2× with DMF. This gives the free Pantebeads, 3A.

EXAMPLE 30

Synthesis of Peptides on Pantebeads

We carried out the synthesis of large amounts peptide-linked Pantebeads on a continuous-flow solid phase peptide synthesizer with double-couplings at each step for fidelity. For synthesis of libraries, the beads were distributed into 96-well polyethylene filter plates (Whatman), and reagent addition was performed manually followed by clamping the filter plate in a sealed clamp (Whatman Combi-Clamp) and agitation on a circular agitator. The plates were evacuated via a filter plate vacuum manifold and washed with solvent addition from above. All couplings, piperidine deprotections, and final TFA deprotection was carried out in the filter plates.

Synthesis on Pantebeads follows standard FMOC peptide synthesis techniques with DIPCDI and HOBt coupling of FMOC protected amino acids and HOBt coupling with pentafluorophenol ester (PFP) activated/FMOC-protected amino acids. (W. C. Chan and P. D. White, "Fmoc Solid Phase Peptide Synthesis: A Practical Approach", Oxford University Press, Oxford, 2000.) Attachment of the first amino acid to the hydroxy-terminal Pantebad resin was carried out by standard technique, with MSNT (1-(mesitylene-2sulphonyl)-3-nitro-1H-1,2,4-triazole) and methylimidazole. FMOC peptide coupling of additional amino acids follows. Final deprotection was carried out by traditional methods with TFA and triisopropylsilane followed by wash 3× with DMF and 3× with buffered water (MOPS pH 7.0).

Although a preferred embodiment of the invention has been described using specific terms, such description is for illustrative purposes only, and it is to be understood that changes and variations may be made without departing from the spirit or scope of the invention as set forth in the following claims.

What is claimed is:

1. A method for the preparation of macrocyclic molecules comprising:
   contacting a purified protein consisting of a thioesterase (TE) domain selected from a polyketide synthase (PKS) or a non-ribosomal peptide synthetase (NRPS) with a substrate for said thioesterase (TE) domain that comprises an activated acyl residue and a pendant nucleophile separated by a linear backbone under conditions conducive to formation of a TE-O-acyl bond such that subsequently the pendant intramolecular nucleophile can displace the TE domain to form the macrocyclic product.

2. A macrocyctization method as in claim 1 wherein the contacting of the protein with a substrate occurs in a medium that comprises at least 90% water.

3. A macrocyclization method as in claim 2, wherein the contacting of the protein with a substrate occurs in a medium that comprises at least 95% water.

4. A macrocyclization method as in claim 2, further comprising non-water component(s) wherein the non-water component(s) is an organic solvent having a sulfoxide, ester, or amide functional group.

5. A macrocyclization method as in claim 1, wherein the contacting of the protein with a substrate occurs in an aqueous solution comprising one or more buffers or other organic or inorganic salts.

6. A macrocyclization method as in claim 1, wherein the pH of the reaction solution is in the range of 5 to 9.

7. A macrocyclization method as in claim 6, wherein the pH of the reaction solution is in the range of 6 to 8.

8. A macrocyclization method as in claim 6, wherein the pH of the reaction solution is 7.

9. A macrocyclization method as in claim 1, wherein the activated acyl residue is an activated ester functional group.

10. A macrocyclization method as in claim 9, wherein the substrate can be represented by the formula:

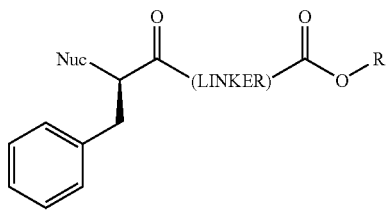

wherein
Nuc is chosen from $NH_2$, OH or SH;
LINKER is a peptidic sequence, a synthetic group comprising alkyl, cycloalkyl, alkenyl, alkynyl, aryl groups or a group that comprises a combination of two or more alkyl, cycloalkyl, alkenyl, alkynyl or aryl group regions and 0 to 3 heteroatoms selected from N, O, and S, or a combination thereof connecting the ester and the 2-(Nuc)-3-phenyl-propionyl residue, the LINKER comprises a linear backbone of at least 14 atoms; and
R is a group that can be represented by the formula:

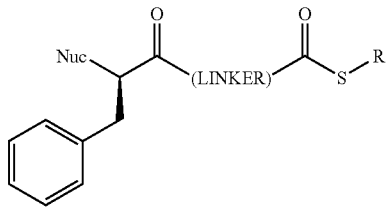

wherein Q is a group having between 4 carbon atoms and 20 carbon atoms and between 0 and 10 hetero atoms selected from N, O or S, which can optionally be tethered to a solid support, where each carbon of the linear backbone may be optionally substituted with 0, 1, or 2 groups selected from $C_{1-6}$alkyl, hydroxy, amino, halogen, $C_{1-6}$alkoxy, or oxo; and
p is an integer from 0 to 2.

11. A macrocyclization method as in claim 1, wherein the activated acyl residue is an activated thioester functional group.

12. A macrocyclization method as in claim 11, wherein the substrate can be represented by the formula:

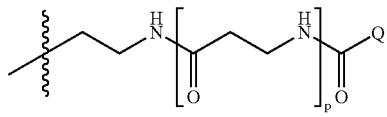

wherein:
Nuc is chosen from $NH_2$, OH or SH;
LINKER is a peptidic sequence, a synthetic group comprising alkyl, cycloalkyl, alkenyl, alkynyl, aryl groups or a group that comprises a combination of two or more alkyl, cycloalkyl, alkenyl, alkynyl or arl group regions and 0 to 3 heteroatoms selected from N, O, and S, or a combination thereof connecting the thioester and the 2-(Nuc)-3-phenyl-propionyl residue, the LINKER comprises a linear backbone of at least 14 atoms; and
R is an optionally substituted $C_{1-12}$ alkyl group or an optionally substituted N-$C_{2-6}$alkanoyl-$C_{2-6}$aminoalkyl group.

13. A macrocyclization method as in claim 12, wherein the substrate is sufficiently polar such that its solubility and that of the resulting macrocycle molecule in the aqueous reaction medium is at least 0.1 g/L.

14. A macrocyclization method as in claim 11, wherein the substrate can be represented by the formula:

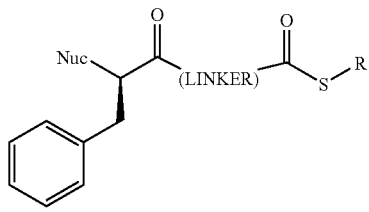

wherein:
Nuc is chosen from $NH_2$, OH or SH;
LINKER is a peptidic sequence, a synthetic group comprising alkyl, cycloalkyl, alkenyl, alkynyl, aryl groups or a group that comprises a combination of two or more alkyl, cycloalkyl, alkenyl, alkynyl or aryl group regions and 0 to 3 heteroatoms selected from N, O, and S, or a combination thereof connecting the thioester and the 2-(Nuc)-3-phenyl-propionyl residue, the LINKER comprises a linear backbone of at least 14 atoms; and
R is a N-$C_{2-6}$alkanoyl-$C_{2-6}$aminoalkyl.

15. A macrocyclization method as in claim 14, wherein the substrate leaving group, SR, is N-acetylcysteamine (SNAC).

16. A macrocyclization method as in claim 12, wherein Nuc is $NH_2$.

17. A macrocyclization method as in claim 12, wherein Nuc is OH.

18. A macrocyclization method as in claim 12, wherein the substrate can be represented by the formula:

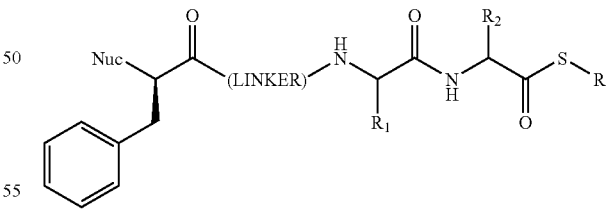

wherein
Nuc is chosen from $NH_2$, OH or SH;
LINKER is a peptidic sequence, a synthetic group comprising alkyl, cycloalkyl, alkenyl, alkynyl, aryl groups or a group that comprises a combination of two or more alkyl, cycloalkyl, alkenyl, alkynyl or aryl group regions and 0 to 3 heteroatoms selected from N, O, or a combination thereof connecting the thioester and the 2-(Nuc)-3-phenyl-propionyl residue, the LINKER comprises a linear backbone of at least 6 atoms;

R is as defined for claim 12; and

R$_1$ and R$_2$ are chosen from the side chain substituents of a synthetic and biosynthetic amino acid residue side chains and each residue can have either D or L stereo-configuration. R$_1$ and R2 are chosen independently and can be the same or different.

19. A macrocyclization method as in claim 18, wherein the substrate is sufficiently polar such that its solubility and that of the resulting macrocyclic molecule in the aqueous reaction medium is at least 0.1 g/L.

20. A macrocyclization method as in claim 18, wherein R$_1$ is a synthetic or biosynthetic amino acid residue side chain substituent including a substituted C$_{1-6}$aminoalkyl group.

21. A macrocyclization method as in claim 20, wherein R$_1$ is L-3-aminopropyl.

22. A macrocyclization method as in claim 11, wherein the substrate can be represented by the formula:

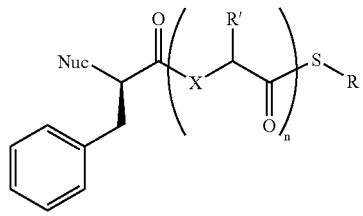

wherein:

Nuc is chosen from NH$_2$ or OH;

n is an integral number greater than or equal to 5;

X is independently chosen from O and NH for each occurrence of X;

R is an optionally substituted N-C$_{2-6}$alkanoyl-C$_{2-6}$aminoalkyl;

R' is independently chosen for each occurrence for R' from the side chain substituents of the synthetic and biosynthetic amino acid residue side chains and each amino acid residue can have either D or L stereoconfiguration.

23. A macrocyclization method as in claim 22, wherein:
Nuc is NH$_2$; and
X is NH for each occurrence of X in the substrate.

24. A macrocyclization method as in claim 22, wherein:
Nuc is NH$_2$; and
X is chosen from O and NH for each occurrence of X in the substrate such that at least one occurrence of X in the substrate is O.

25. A macrocyclization method as in claim 22, wherein:
Nuc is OH; and
X is NH for each occurrence of X in the substrate.

26. A method as in claim 22, wherein n is between 5 and 15 inclusive.

27. A method as in claim 22, wherein at least one occurrence of R' is 3-aminopropyl.

28. A macrocyclization method according to claim 12, wherein the substrate that comprises at least one non-peptidic spacer can be represented by the formula:

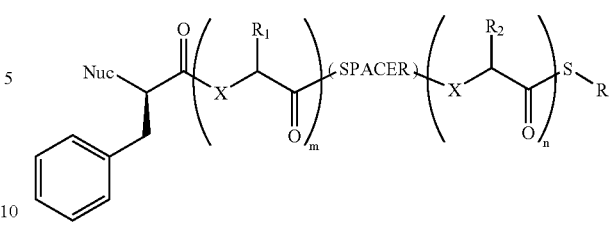

wherein:

Nuc is chosen from NH$_2$ or OH;

m and n are non-negative integers;

X is independently chosen for each occurrence of X in the formula to be either O or NH;

SPACER is a group of atoms or functional group residues that are not amino acid residues or depsi residues that comprise z atoms in the linear backbone of the substrate;

z is an integral number greater than or equal to 4;

the sum of z+3m+3n is between 12 and 36; and

R$_1$ and R$_2$ are chosen from the side chain substituents of a synthetic and biosynthetic amino acid residue side chains and each residue can have either D or L stereo-configuration.

29. A macrocyclization method as in claim 28, wherein the substrate is sufficiently polar such that its solubility and that of the resulting macrocyclic molecule in the aqueous reaction medium is at least 0.1 g/L.

30. A macrocyclization method as in claim 28, wherein z is 6 to 24.

31. A macrocyclization method as in claim 28, wherein the non-peptidic SPACER(s) comprises one or more of the following substituted groups such that the total number of atoms, z, in the linear backbone of the SPACER is greater than 6: C$_{3-12}$-alkyl, C$_{3-12}$-alkenyl, C$_{3-12}$-alkynyl, C$_{3-7}$cycloalkyl, C$_{3-7}$heteroalicyclic, aryl, heteroaryl, amine, C$_{1-12}$alkylamino, amide, ester, ketone, sulfoxide, ether, thioether, imine, sulfone.

32. A macrocyclization method as in claim 28, wherein the non-peptidic SPACER(s) comprises one or more of the following functional groups such that the total number of atoms, z, in the linear backbone of the SPACER is greater than 6: α,ω-alkandiyl, α,ω-alkane diol, α,ω-alkane diamine, ω-(1-alkanol)amine, ω-hydroxyalkanoate or ω-aminoalkanoate such that two or more functional groups are linked by bonds chosen from the group of ether, amine, amide or ester bonds where each bond is independently chosen for each linkage.

33. A macrocyclization method as in claim 32, wherein the non-peptidic SPACER comprises one or more of the following functional groups linked together by either an amide or ester bond each bond being independently chosen at each occurrence: glycine, glycolate, O-(2-aminoethyl) glycolate, O-(2-ethanol)glycolate, O-(2-(2-aminoethoxy) ethyl)glycolate, O-(diethylene glycol)glycolate.

34. A macrocyclization method according to claim 1, wherein the substrate is represented by the formula:

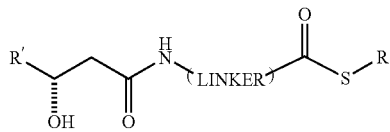

wherein:
LINKER is a peptidic sequence, synthetic group comprising alkyl, cycloalkyl, alkenyl, alkynyl, aryl groups or a group that comprises a combination of two or more alkyl, cycloalkyl, alkenyl, alkynyl or aryl group regions and 0 to 3 heteroatoms selected from N, O, and S, or a combination thereof connecting the thioester and the 2-(Nuc)-3-phenyl-propionyl residue, the LINKER comprises a linear backbone of at least 14 atoms;

R is an optionally substituted $C_{1-12}$ alkyl group; and

R' is a $C_{1-18}$ alkyl group or a lipophilic group.

35. A method for successive dimerization and macrocyclization of a peptide or modified peptide, the method comprising the steps of:
elongating a peptide or modified peptide substrate, which can not be cyclized by purified protein consisting of a TE domain from a polyketide synthase (PKS) or a non-ribosomal peptide synthetase (NRPS), by contacting said TE domain with a first said peptide or modified peptide substrate under conditions conducive to formation of a TE-O-acyl substrate intermediate such that subsequently an intermolecular recognition element nucleophile from a second identical peptide or modified peptide substrate can displace the TE domain to form an elongated intermediate substrate homodimer;
repeating the elongating step until the elongated intermediate substrate oligomer is of sufficient length to undergo macrocyclization by said TE domain; and
allowing said elongated intermediate substrate to stay in the reaction media until the cyclization reaction is completed by the TE domain to form the macrocyclic product, thereby producing a macrocyclic peptide or modified peptide.

36. A method as in claim 35, wherein the contacting of the protein with a substrate occurs in a medium that comprises at least 90% water.

37. A method as in claim 35, wherein the contacting of the protein with a substrate occurs in a medium that comprises at least 95% water.

38. A method as in claim 35, further comprising a non-water component(s) wherein the non-water component(s) is an organic solvent having a sulfoxide, ester, or amide functional group.

39. A method as in claim 35, wherein the contacting of the protein with a substrate occurs in an aqueous solution comprising one or more buffers or other organic or inorganic salts.

40. A method as in claim 35, wherein the pH of the reaction solution is in the range of 5 to 9.

41. A method as in claim 40, wherein the pH of the reaction solution is in the range of 6 to 8.

42. A method as in claim 40, wherein the pH of the reaction solution is 7.

43. A method as in claim 35, with a substrate according to the formula:

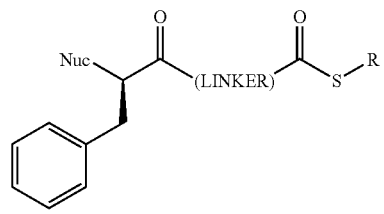

wherein:
Nuc is chosen from $NH_2$ or OH;
LINKER is a group of atoms or functional group residues connecting the thioester and the 2-(Nuc)-3-phenyl-propionyl residue and LINKER comprises a linear not more than 14 atoms; and
R is N-$C_{24}$alkanoyl$C_{2-6}$aminoalkyl group.

44. A method as in claim 43, wherein the substrate is sufficiently polar such that its solubility and that of the resulting macrocyclic molecule in the aqueous reaction medium is at least 0.1 g/L.

45. A method as in claim 43, wherein the substrate leaving group, SR, is N-acetylcysteamine (SNAC).

46. A method as in claim 43, wherein the substrate Nuc is $NH_2$.

47. A method as in claim 43, wherein the substrate Nuc is OH.

48. A method as in claim 43, wherein the substrate can be represented by the formula:

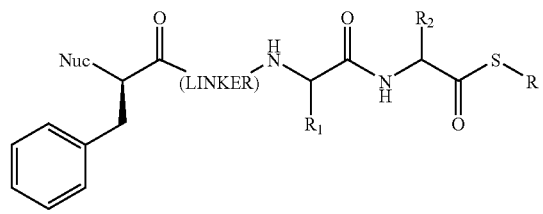

wherein
Nuc is chosen from $NH_2$ or OH;
LINKER is a group of atoms or functional group residues connecting the thioester and the 2-(Nuc)-3-phenyl-propionyl residue, the LINKER comprises a linear backbone of not more that 9 atoms;
R is as defined for claim 43; and
$R_1$ and $R_2$ are chosen from side chain substituents of the synthetic and biosynthetic amino acid residue side chains and each residue can have either D or L stereo-configuration, $R_1$ and $R_2$ are chosen independently and can be the same or different.

49. A method as in claim 48, wherein $R_1$ is a synthetic or biosynthetic amino acid residue side chain substituent including a substituted $C_{1-6}$aminoalkyl group.

50. A method as in claim 49, wherein $R_1$ is L-3-aminopropyl.

51. A method as in claim 43, wherein the substrate can be represented by the formula:

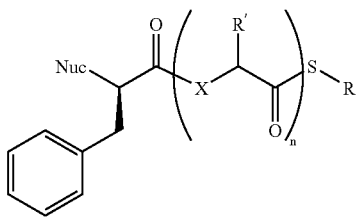

wherein:
R is as defined in claim 43;
Nuc is chosen from NH$_2$ or OH;
n is an integral number greater than or equal to 5;
X is independently chosen for each occurrence of X from O and NH; and
R' is independently chosen for each occurrence for R' from the side chain substituents of the synthetic and biosynthetic amino acid residue side chains and each amino acid residue can have either D or L stereoconfiguration.

52. A method as in claim 51, wherein:
Nuc is NH$_2$; and
X is NH for each occurrence of X in the substrate.

53. A method as in claim 51, wherein:
Nuc is NH$_2$; and
X is chosen from O and NH for each occurrence of X in the substrate such that at least one occurrence of X in the substrate is O.

54. A method as in claim 51, wherein:
Nuc is OH; and
X is NH for each occurrence of X in the substrate.

55. A method as in claim 51, wherein at least one occurrence of R' is 3-aminopropyl.

56. A method for the preparation of macrocyclic molecules comprising:
contacting purified protein consisting of a TE domain from a polyketide synthase (PKS) or a non-ribosomal peptide synthetase (NRPS) with a substrate that comprises an activated acyl residue and a pendant nucleophile separated by a linear backbone under conditions conducive to formation of a TE-O-acyl bond such that subsequently the pendant intramolecular nucleophile can displace the TE domain to form the macrocyclic product;
wherein the substrate can be represented by the formula A:

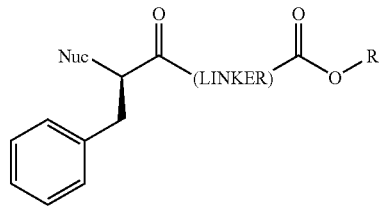

wherein
Nuc is chosen from NH$_2$, OH or SH;
LINKER is a peptidic sequence, a synthetic group comprising alkyl, cycloalkyl, alkenyl, alkynyl, aryl groups or a group that comprises a combination of two or more alkyl, cycloalkyl, alkenyl, alkynyl or aryl group regions and 0 to 3 heteroatoms selected from N, O, and S, or a combination thereof connecting the ester and the 2-(Nuc)-3-phenyl-propionyl residue, the LINKER comprises a linear backbone of at least 14 atoms; and
R is a group that can be represented by the formula:

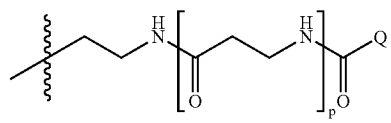

wherein Q is a group having between 4 carbon atom and 20 carbon atoms and between 0 and 10 hetero atoms selected from N, O or S, which can optionally be tethered to a solid support, where each carbon of the linear backbone may be optionally substituted with 0, 1, or 2 groups selected from C$_{1-6}$alkyl, hydroxy, amino, halogen, C$_{1-6}$alkoxy, or oxo; and
p is an integer from 0 to 2: or
wherein the substrate can be represented by the formula B: B.

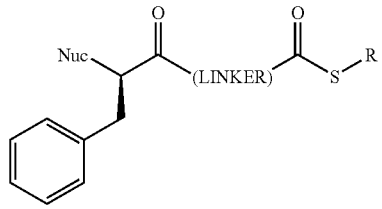

wherein:
Nuc is chosen from NH2, OH or SH;
LINKER is a peptidic sequence, a synthetic group comprising alkyl, cycloalkyl, alkenyl, alkynyl, awl groups or a group that comprises a combination of two or more alkyl, cycloalkyl, alkenyl, alkynyl or aryl group regions and 0 to 3 heteroatoms selected from N, O, and S, or a combination thereof connecting the thioester and the 2-(Nuc)-3-phenyl-propionyl residue, the LINKER comprises a linear backbone of at least 14 atoms; and
R is an optionally substituted C$_{1-12}$ alkyl group or an optionally substituted N-C$_{2-6}$alkanoyl-C$_{2-6}$aminoalkyl group.

* * * * *